(12) United States Patent
Singh et al.

(10) Patent No.: US 7,645,339 B2
(45) Date of Patent: *Jan. 12, 2010

(54) SILICON-CONTAINING LAYER DEPOSITION WITH SILICON COMPOUNDS

(75) Inventors: Kaushal K. Singh, Santa Clara, CA (US); Paul B. Comita, Menlo Park, CA (US); Lance A. Scudder, San Jose, CA (US); David K. Carlson, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 411 days.

This patent is subject to a terminal disclaimer.

(21) Appl. No.: 11/549,033

(22) Filed: Oct. 12, 2006

(65) Prior Publication Data
US 2007/0240632 A1 Oct. 18, 2007

Related U.S. Application Data

(63) Continuation of application No. 10/688,797, filed on Oct. 17, 2003, now abandoned.

(60) Provisional application No. 60/419,376, filed on Oct. 18, 2002, provisional application No. 60/419,426, filed on Oct. 18, 2002, provisional application No. 60/419,504, filed on Oct. 18, 2002.

(51) Int. Cl.
*C30B 21/04* (2006.01)

(52) U.S. Cl. .............................. 117/89; 117/104; 117/15

(58) Field of Classification Search ................. 117/935, 117/104, 105, 86
See application file for complete search history.

(56) References Cited

U.S. PATENT DOCUMENTS

| | | | |
|---|---|---|---|
| 4,690,830 A | 9/1987 | Dickson et al. | |
| 4,830,890 A | 5/1989 | Kanai | |
| 4,834,831 A | 5/1989 | Nishizawa et al. | |
| 4,990,374 A | 2/1991 | Keeley et al. | |
| 5,112,439 A | 5/1992 | Reisman et al. | |
| 5,273,930 A | 12/1993 | Steele et al. | |
| 5,294,286 A | 3/1994 | Nishizawa et al. | |
| 5,372,860 A | 12/1994 | Fehlner et al. | |
| 5,374,570 A | 12/1994 | Nasu et al. | |
| 5,469,806 A | 11/1995 | Mochizuki et al. | |
| 5,480,818 A | 1/1996 | Matsumoto et al. | |
| 5,503,875 A | 4/1996 | Imai et al. | |
| 5,521,126 A | 5/1996 | Okamura et al. | |
| 5,527,733 A | 6/1996 | Nishizawa et al. | |
| 5,604,151 A | 2/1997 | Goela et al. | |
| 5,674,304 A | 10/1997 | Fukada et al. | |
| 5,693,139 A | 12/1997 | Nishizawa et al. | |
| 5,796,116 A | 8/1998 | Nakata et al. | |
| 5,807,792 A | 9/1998 | Ilg et al. | |
| 5,906,680 A | 5/1999 | Meyerson | |
| 5,916,365 A | 6/1999 | Sherman et al. | |
| 6,025,627 A | 2/2000 | Forbes et al. | |
| 6,027,705 A | 2/2000 | Kitsuno et al. | |
| 6,042,654 A | 3/2000 | Comita et al. | |
| 6,124,158 A | 9/2000 | Dautartas et al. | |
| 6,144,060 A | 11/2000 | Park et al. | |
| 6,159,852 A | 12/2000 | Nuttall et al. | |
| 6,200,893 B1 | 3/2001 | Sneh | |
| 6,207,487 B1 | 3/2001 | Kim et al. | |
| 6,232,196 B1 | 5/2001 | Raaijmakers et al. | |
| 6,270,572 B1 | 8/2001 | Kim et al. | |
| 6,284,646 B1 | 9/2001 | Leem | |
| 6,284,686 B1 | 9/2001 | Marlor | |
| 6,287,965 B1 | 9/2001 | Kang et al. | |
| 6,291,319 B1 | 9/2001 | Yu et al. | |
| 6,305,314 B1 | 10/2001 | Sneh et al. | |

(Continued)

FOREIGN PATENT DOCUMENTS

EP 0 296 702 4/1988

(Continued)

OTHER PUBLICATIONS

Argarwal, et al. "Challenges in Integrating the High-K Gate Dielectric Film to the Conventional CMOS Process Flow," Mat. Sec. Soc. Sump. Proc. vol. 670 (2001), pp. K2.1.1-K2.1.11.
Bedair, "Atomic Layer Epitaxy Deposition Processes," J. Vac. Sci. Technol. B., vol. 12, No. 1, Jan./Feb. 1994, 7 pages.
Choi, et al. "The Effect of Annealing on Resistivity of Low Pressure Chemical Vapor Deposited Titanium Diboride," J. Appl. Phys. 69(11), Jun. 1, 1991, pp. 7853-7861.
Choi, et al. "Stability of $TiB_2$ as a Diffusion Barrier on Silicon," J. Electrochem. Soc., vol. 138, No. 10, Oct. 1991, pp. 3062-3067.
Derbyshire, "Applications of Integrated Processing," Solid State Technology, Dec. 1994, pp. 45-49.

(Continued)

*Primary Examiner*—Robert M Kunemund
(74) *Attorney, Agent, or Firm*—Townsend and Townsend and Crew, LLP

(57) ABSTRACT

Embodiments of the invention relate to methods for depositing silicon-containing materials on a substrate. In one example, a method for selectively and epitaxially depositing a silicon-containing material is provided which includes positioning and heating a substrate containing a crystalline surface and a non-crystalline surface within a process chamber, exposing the substrate to a process gas containing neopentasilane, and depositing an epitaxial layer on the crystalline surface. In another example, a method for blanket depositing a silicon-containing material is provide which includes positioning and heating a substrate containing a crystalline surface and feature surfaces within a process chamber and exposing the substrate to a process gas containing neopentasilane and a carbon source to deposit a silicon carbide blanket layer across the crystalline surface and the feature surfaces. Generally, the silicon carbide blanket layer contains a silicon carbide epitaxial layer selectively deposited on the crystalline surface.

31 Claims, No Drawings

U.S. PATENT DOCUMENTS

| | | |
|---|---|---|
| 6,335,280 B1 | 1/2002 | van der Jeugd |
| 6,342,277 B1 | 1/2002 | Sherman |
| 6,348,420 B1 | 2/2002 | Raaijmakers et al. |
| 6,352,945 B1 | 3/2002 | Matsuki et al. |
| 6,358,829 B2 | 3/2002 | Yoon et al. |
| 6,383,955 B1 | 5/2002 | Matsuki et al. |
| 6,384,437 B1 | 5/2002 | Tee et al. |
| 6,391,785 B1 | 5/2002 | Satta et al. |
| 6,391,803 B1 | 5/2002 | Kim et al. |
| 6,399,491 B2 | 6/2002 | Jeon et al. |
| 6,410,463 B1 | 6/2002 | Matsuki |
| 6,451,119 B2 | 9/2002 | Sneh et al. |
| 6,458,718 B1 | 10/2002 | Todd |
| 6,468,924 B2 | 10/2002 | Lee et al. |
| 6,489,241 B1 | 12/2002 | Thilderkvist et al. |
| 6,492,283 B2 | 12/2002 | Raaijmakers et al. |
| 6,503,799 B2 | 1/2003 | Horita et al. |
| 6,511,539 B1 | 1/2003 | Raaijmakers |
| 6,534,395 B2 | 3/2003 | Werkhoven et al. |
| 6,544,900 B2 | 4/2003 | Raaijmakers et al. |
| 6,559,520 B2 | 5/2003 | Matsuki et al. |
| 6,562,720 B2 | 5/2003 | Thilderkvist et al. |
| 6,630,413 B2 | 10/2003 | Todd |
| 6,632,279 B1 | 10/2003 | Ritala et al. |
| 6,770,134 B2 | 8/2004 | Maydan et al. |
| 6,794,713 B2 | 9/2004 | Mizushima et al. |
| 6,797,558 B2 | 9/2004 | Nuttall et al. |
| 6,821,825 B2 | 11/2004 | Todd |
| 6,905,542 B2 | 6/2005 | Samoilov et al. |
| 6,916,398 B2 | 7/2005 | Chen et al. |
| 6,926,926 B2 | 8/2005 | Cho et al. |
| 2001/0000866 A1 | 5/2001 | Sneh et al. |
| 2001/0020712 A1 | 9/2001 | Raaijmakers et al. |
| 2001/0024387 A1 | 9/2001 | Raaijmakers et al. |
| 2001/0024871 A1 | 9/2001 | Yagi |
| 2001/0028924 A1 | 10/2001 | Sherman et al. |
| 2001/0034123 A1 | 10/2001 | Jeon et al. |
| 2001/0041250 A1 | 11/2001 | Sneh et al. |
| 2001/0046567 A1 | 11/2001 | Matsuki et al. |
| 2001/0055672 A1 | 12/2001 | Todd |
| 2002/0000598 A1 | 1/2002 | Kang et al. |
| 2002/0016084 A1 | 2/2002 | Todd |
| 2002/0031618 A1 | 3/2002 | Sherman |
| 2002/0047151 A1 | 4/2002 | Kim et al. |
| 2002/0052077 A1 | 5/2002 | Tee et al. |
| 2002/0074588 A1 | 6/2002 | Lee |
| 2002/0076837 A1 | 6/2002 | Hujanen et al. |
| 2002/0090818 A1 | 7/2002 | Thilderkvist et al. |
| 2002/0093042 A1 | 7/2002 | Oh et al. |
| 2002/0098627 A1 | 7/2002 | Pomarede et al. |
| 2002/0127841 A1 | 9/2002 | Horita et al. |
| 2002/0145168 A1 | 10/2002 | Bojarczuk, Jr. et al. |
| 2002/0155722 A1 | 10/2002 | Satta et al. |
| 2002/0168868 A1 | 11/2002 | Todd |
| 2002/0172768 A1 | 11/2002 | Endo et al. |
| 2002/0173113 A1 | 11/2002 | Todd |
| 2002/0173130 A1 | 11/2002 | Pomerede et al. |
| 2002/0197831 A1 | 12/2002 | Todd et al. |
| 2002/0197881 A1 | 12/2002 | Ramdani et al. |
| 2003/0013320 A1 | 1/2003 | Kim et al. |
| 2003/0015764 A1 | 1/2003 | Raaijmakers et al. |
| 2003/0022528 A1 | 1/2003 | Todd |
| 2003/0032281 A1 | 2/2003 | Werkhoven et al. |
| 2003/0036268 A1 | 2/2003 | Brabant et al. |
| 2003/0049942 A1 | 3/2003 | Haukka et al. |
| 2003/0060057 A1 | 3/2003 | Raaijmakers et al. |
| 2003/0072975 A1 | 4/2003 | Shero et al. |
| 2003/0082300 A1 | 5/2003 | Todd et al. |
| 2003/0089308 A1 | 5/2003 | Raaijmakers |
| 2003/0089942 A1 | 5/2003 | Bhattacharyya |
| 2003/0101927 A1 | 6/2003 | Raaijmakers |
| 2003/0116804 A1 | 6/2003 | Visokay et al. |
| 2003/0129826 A1 | 7/2003 | Werkhoven et al. |
| 2003/0143841 A1 | 7/2003 | Yang et al. |
| 2003/0160277 A1 | 8/2003 | Bhattacharyya |
| 2003/0173586 A1 | 9/2003 | Moriwaki et al. |
| 2003/0185980 A1 | 10/2003 | Endo |
| 2003/0188682 A1 | 10/2003 | Tois et al. |
| 2003/0189208 A1 | 10/2003 | Law et al. |
| 2003/0194853 A1 | 10/2003 | Jeon |
| 2003/0197831 A1 | 10/2003 | Kim |
| 2003/0205729 A1 | 11/2003 | Basceri et al. |
| 2004/0033674 A1 | 2/2004 | Todd |
| 2004/0226911 A1 | 11/2004 | Dutton et al. |
| 2004/0253776 A1 | 12/2004 | Hoffmann et al. |
| 2005/0079691 A1 | 4/2005 | Kim et al. |

FOREIGN PATENT DOCUMENTS

| | | |
|---|---|---|
| EP | 1 150 345 A2 | 10/2001 |
| JP | 58-098917 | 6/1983 |
| JP | 62-171999 | 2/1987 |
| JP | 63-062313 | 3/1988 |
| JP | 63234513 | 9/1988 |
| JP | 01-083510 | 3/1989 |
| JP | 1-143221 | 6/1989 |
| JP | 1-270593 | 10/1989 |
| JP | 2-172895 | 7/1990 |
| JP | 3-286522 | 12/1991 |
| JP | 5-047665 | 2/1993 |
| JP | 5-102189 | 4/1993 |
| JP | 5-251339 | 9/1993 |
| JP | 6-196809 | 7/1994 |
| JP | 07-300649 | 11/1995 |
| JP | 2001-189312 | 5/2001 |
| JP | 2001-111000 | 12/2002 |
| WO | WO 98/20524 A1 | 5/1998 |
| WO | WO 00/16377 A2 | 3/2000 |
| WO | WO 00/54320 A1 | 9/2000 |
| WO | WO 01/15220 A1 | 3/2001 |
| WO | WO 01/17692 A1 | 3/2001 |
| WO | WO 01/29893 A1 | 4/2001 |
| WO | WO 01/40541 A1 | 6/2001 |
| WO | WO 01/41544 A2 | 6/2001 |
| WO | WO 01/66832 A2 | 9/2001 |
| WO | WO 02/064853 A2 | 8/2002 |
| WO | WO 02/065508 A2 | 8/2002 |
| WO | WO 02/065516 A2 | 8/2002 |
| WO | WO 02/065517 A2 | 8/2002 |
| WO | WO 02/065525 A1 | 8/2002 |
| WO | WO 02/080244 A2 | 10/2002 |
| WO | WO 02/097864 A2 | 12/2002 |

OTHER PUBLICATIONS

Elers, et al. "NbCI$_5$ as a Precursor in Atomic Layer Epitaxy," Applied Surface Science 82/83 (1994), pp. 468-474.

George, et al., "Surface Chemistry for Atomic Layer Growth," J. Phys. Chem. (1996) 100, pp. 13121-13131.

Hwang, et al. "Nanometer-Size $\alpha$-PbO$_2$-type TiO$_2$ in Garnet: A Thermobarometer for Ultrahigh-Pressure Metamorphism," (Apr. 14, 2000), vol. 288, pp. 321-324.

Jeong, et al. "Plasma-assisted Atomic Layer Growth of High-Quality Aluminum Oxide Thin Films," Japanese Journal of Applied Physics 1, vol. 40, (2001), pp. 285-289.

Jeong, et al. "Growth and Characterization of Aluminum Oxide Al$_2$O$_3$ Thin Films by Plasma-assisted Atomic Layer Controlled Deposition," J. Korean Inst. Met. Mater., vol. 38, (2000), pp. 1395-1399.

Imai, et al., "A Novel Atomic Layer Epitaxy Method of Silicon," Journal of Applied Physics vol. 30, No. 12B, Dec. 1991, pp. 3646-3651.

Lee, et al. "Cyclic Technique for the Enhancement of Highly Oriented Diamond Film Growth," Thin Solid Films 303 (1997), pp. 264-269.

Lubben, et al. "Mechanisms and Kinetics of Si Atomic-layer Epitaxy on Si(001)2X1 from $Si_2H_6$," Journal of Vacuum Science Technology A 9 (6), Nov./Dec. 1991, pp. 3003-3011.

Min, et al. "Metal-organic Atomic-layer Deposition of Titanium-silicon-nitride Films," Applied Physics Letters, vol. 75, No. 11 (Sep. 11, 1999), pp. 1521-1523.

Min, et al. "Chemical Vapor Deposition of Ti-Si-N Films with Alternating Source Supply," Material Research Society Symposium Proceedings, vol. 564 (1999), pp. 207-211.

Paranjpe, et al. "Atomic Layer Deposition of $AlO_x$ for Thin Film Head Gap Applications," Journal of Electrochemical Society, vol. 148, No. 9, (2001), pp. G465-G471.

Ritala, et al. "Atomic Layer Deposition of Oxide Thin Films with Metal Alkoxides as Oxygen Sources," Science vol. 288, (Apr. 14, 2000), pp. 319-321.

Suda, et al. "Adsorption and Thermal Dissociation of Disilane ($Si_2H_6$) on Si(100)2X1," Journal of Vacuum Science Technology, A8 (1), Jan./Feb. 1990, pp. 61-67.

Kamins, et al. "Kinetics of Selective Epitaxial Deposition of $Si_{1-x}Ge_x$", Applied Physics Letters, American Institute pf Physics. vol. 61, No. 6, (Aug. 10, 1992), pp. 669-671.

Menon, et al. "Loading Effect in SiGe Layers Grown by Dichlorosilane- and Silane-based Epitaxy", Journal of Applied Physics, American Institute of Physics. vol. 90, No. 9, (Nov. 1, 2001), pp. 4805-4809.

Sedgwick, et al. "Selective SiGe and Heavily as Doped Si Deposited at Low Temperature by Atmospheric Pressure Chemical Vapor Deposition", Journal of Vacuum Science and Technology: Part B, vol. 11, No. 3, (May 1, 1993), pp. 1124-1128.

Uchino, et al. "A Raised Source/Drain Technology Using In-situ P-doped SiGe and B-doped Si for 0.1 µm CMOS ULSIs", IEEE, IEDM (1997), pp. 479-482.

Moore, D.L., et al., "Reaction of Hydrogen Peroxide With Organosilanes Under Chemical Vapor Deposition Conditions," Royal Society of Chemistry, J. Chem. Soc., Dalton Trans., (2000) (16), pp. 2673-2677.

Applied Materials has been notified by Dow Corning that it asserts one or more unnamed employees of Dow Corning contributed to the subject matter claimed in Applicant's pending application. Dow Corning has not identified the names of the individual(s) that it asserts may have contributed to the invention.

Applied Materials does not believe Dow Corning's assertion regarding its employees' sole or joint inventorship has merit, and believes in good faith that Kaushal K. Singh, Paul B. Comita, Lance A. Scudder, and David K. Carlson are the true and first inventors of all of the claimed subject matter in their pending patent application.

Applied Materials is bringing this information to the Examiner's attention to satify its duty under the Rules, and further to request the Examiner to consider whether, in his judgment, a more comprehensive interference search for any pending application by Dow Corning should be conducted prior to issuing the currently-pending claims. There is no additional attachment to this form.

SILICON-CONTAINING LAYER DEPOSITION WITH SILICON COMPOUNDS

CROSS-REFERENCE TO RELATED APPLICATIONS

This application is a continuation of U.S. Ser. No. 10/688,797, filed Oct. 17, 2003 now abandoned, which claims benefit of U.S. Ser. No. 60/419,376, filed Oct. 18, 2002, U.S. Ser. No. 60/419,426, filed Oct. 18, 2002, and U.S. Ser. No. 60/419,504, filed Oct. 18, 2002, which are herein incorporated by reference in their entirety.

BACKGROUND OF THE INVENTION

1. Field of the Invention

Embodiments of the invention generally relate to deposition of silicon-containing films, and more particularly to silicon compound compositions and related processes to deposit silicon-containing films.

2. Description of the Related Art

Atomic layer epitaxy (ALE) offers meticulous control of film thickness by growing single atomic layers upon a crystal lattice. ALE is employed to develop many group IV semiconductor materials, such as silicon, germanium, silicon germanium, silicon carbon and silicon germanium carbon. Silicon based materials, produced via ALE, are of interest for use as semiconductor materials. The silicon based materials can include germanium and/or carbon at selectable concentrations and are grown as polysilicon, amorphous or monocrystalline films. Silicon-ALE, in which a silicon-containing film is epitaxial grown, consists of two steps.

A monolayer of partially decomposed source gas molecules (e.g., $SiH_4$ or $SiH_2Cl_2$) is adsorbed over the substrate or surface. The adsorbate may consists of a silicon atom and at least another kind of atom or group bonded with silicon, such as chlorine, hydrogen or methyl (e.g., $SiCl_n$, $SiH_n$ or $H_{4-n}SiMe_n$, where n=1-4). The adsorbate decomposes to form adatoms of silicon on the surface. The adatoms migrate or diffuse on the surface to an empty lattice site of the silicon crystal. The crystal continues to form and grow as adatoms are generated on the crystalline surface and incorporated into the lattice. By-product removal is achieved and a new surface is created on the monolayer. The monolayer growth in the next cycle is made possible.

Source gases used during silicon deposition include lower silanes (e.g., silane, dichlorosilane and tetrachlorosilane) as well as higher silanes (e.g., disilane, hexachlorodisilane and trisilane). Silane and dichlorosilane are the most common source gases used during Si-ALE, such as described in U.S. Ser. No. 09/963,411, published as U.S. Pub. No. 2002-0052077, and issued as U.S. Pat. No. 6,384,437. These lower silanes require the substrate to be maintained at high temperatures, often in the range of 800-1,000° C. Higher silanes are utilized as source gases to lower the temperature needed during Si-ALE. Disilane is used to grow silicon by ultraviolet-photostimulated ALE in the temperature range of 180-400° C., as demonstrated by Suda, et al., *J. Vac. Sci. Technol. A*, 8 (1990) 61., as well as by Lubben, et al., *J. Vac. Sci. Technol. A*, 9 (1991) 3003. Furthermore, trisilane is used as a source gas during Si-ALE at about 380° C., as reported by Imai, et al., *Jpn. J. Appl. Phys.*, 30 (1991) 3646.

Si-ALE with supplemental etchants has also been realized. Horita, et al., U.S. Ser. No. 09/991,959, published as U.S. Pub. No. 2002-0127841, and issued as U.S. Pat. No. 6,503,799, teaches the combination of dichlorosilane and hydrogen chloride to accomplish selective silicon growth. Supplemental etchants are generally halogenated and/or radical compounds (e.g., HCl or .Cl) that necessitate high reactivity. Therefore, hazardous and toxic conditions are often associated with etchant use.

Therefore, there is a need to provide silicon-containing compounds that provide both a source chemical for silicon deposition and a source chemical as an etchant. The silicon-containing compounds should be versatile to be applied in a variety of silicon deposition techniques.

SUMMARY OF THE INVENTION

In one embodiment, the invention generally provides a method for depositing a silicon-containing film, comprising delivering a silicon compound to a substrate surface and reacting the silicon compound to deposit the silicon-containing film on the substrate surface. The silicon compound comprises a structure:

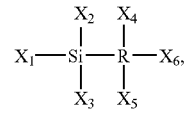

wherein $X_1$-$X_6$ are independently hydrogen or halogen, R is carbon, silicon or germanium and $X_1$-$X_6$ comprise at least one hydrogen and at least one halogen.

In another embodiment, the invention generally provides a composition of matter comprising a structure:

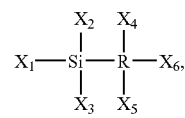

wherein $X_1$-$X_6$ are independently hydrogen or halogen, R is carbon, silicon or germanium and $X_1$-$X_6$ comprise at least one hydrogen and at least one halogen and the proviso that R is not carbon when $X_4$, $X_5$ and $X_6$ are fluorine.

In another embodiment, the invention generally provides a composition of matter comprising a structure:

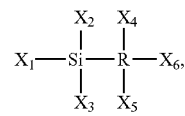

wherein $X_1$-$X_6$ are independently hydrogen or halogen and R is germanium.

In another embodiment, the invention generally provides a method for depositing a silicon-containing film, comprising delivering a silicon compound to a substrate surface and reacting the silicon compound to deposit the silicon-containing film on the substrate surface. The silicon compound comprising structures:

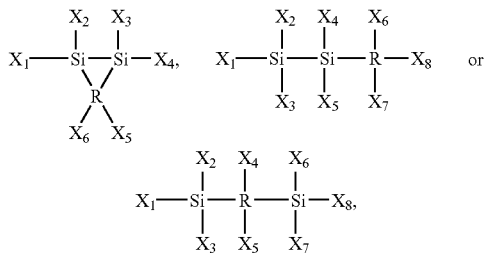

wherein $X_1$-$X_8$ are independently hydrogen or halogen, R is carbon, silicon or germanium and $X_1$-$X_8$ comprise at least one halogen.

In another embodiment, the invention generally provides a composition of matter comprising a structure:

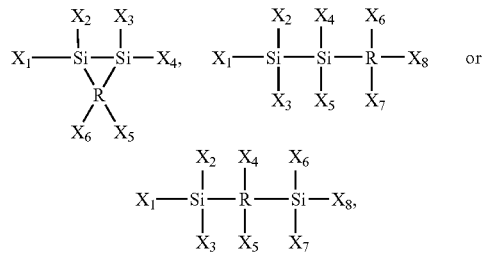

wherein $X_1$-$X_8$ are independently hydrogen or halogen, R is carbon, silicon or germanium and $X_1$-$X_8$ comprise at least one halogen.

In another embodiment, the invention generally provides a composition of matter comprising structures:

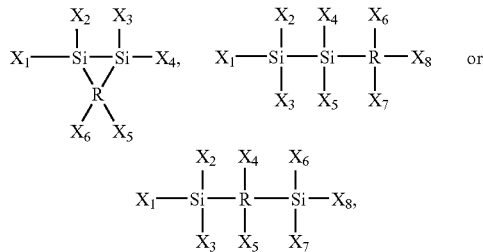

wherein $X_1$-$X_8$ are independently hydrogen or halogen and R is germanium.

In another embodiment, the invention generally provides a method for depositing a silicon-containing film by delivering a silicon compound to a substrate surface and reacting the silicon compound to deposit the silicon-containing film on the substrate surface. In some embodiments, the silicon compound comprises three silicon atoms, fourth atom of carbon, silicon or germanium and atoms of hydrogen or halogen with at least one halogen. In other embodiments, the silicon compound comprises four silicon atoms, fifth atom of carbon, silicon or germanium and atoms of hydrogen or halogen with at least one halogen. In some embodiments, the silicon-containing film is selected from the group consisting of silicon, silicon germanium, silicon carbon and silicon germanium carbon.

In another embodiment, the invention generally provides a composition of matter comprising three silicon atoms, fourth atom of carbon, silicon or germanium and atoms of hydrogen or halogen with at least one halogen. In other embodiments, the invention generally provides a composition of matter comprising four silicon atoms, fifth atom of carbon, silicon or germanium and atoms of hydrogen and/or halogen.

DETAILED DESCRIPTION

Embodiments of the invention pertain to processes for epitaxially depositing silicon-containing films of a desired thickness on a substrate. The processes generally include silicon compounds that contain silicon sources, as well as etchant sources, within the same molecule. A silicon source is a compound that includes from at least one silicon atom and to five silicon atoms. An etchant source is a compound that includes at least one functional group with etchant characteristics. In some embodiments, molecules are used that also contain silicon germanium sources or silicon carbon sources.

In one aspect, embodiments of the invention relate to silicon compounds comprising a structure:

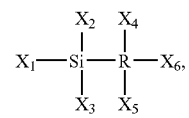

wherein $X_1$-$X_6$ are independently hydrogen or halogen, R is carbon, silicon or germanium and $X_1$-$X_6$ comprise at least one hydrogen and at least one halogen.

Silicon sources have formulas such as $Cl_3SiSiCl_2H$, $Cl_3SiSiClH_2$, $Cl_3SiSiH_3$, $HCl_2SiSiH_3$, $H_2ClSiSiH_3$, $HCl_2SiSiCl_2H$ and $H_2ClSiSiClH_2$. Other silicon sources are derived by the replacement of at least one H-atom and/or at least one Cl-atom with another halogen, such as fluorine. Therefore, silicon sources may have chemical formulas such as $Cl_3SiSiF_2H$, $F_3SiSiClH_2$, $F_3SiSiH_3$, $F_3SiSiCl_3$, $HFClSiSiF_3$, $H_2ClSiSiH_3$, $FCl_2SiSiF_2H$ and $H_2ClSiSiClF_2$. Other similarly halogenated silicon sources enable the processes.

Silicon germanium sources may have formulas such as $Cl_3SiGeCl_3$, $H_3SiGeH_3$, $Cl_3SiGeCl_2H$, $Cl_3SiGeClH_2$, $Cl_3SiGeH_3$, $HCl_2SiGeH_3$, $H_2ClSiGeH_3$, $HCl_2SiGeCl_2H$, $H_2ClSiGeClH_2$, $Cl_3GeSiCl_2H$, $Cl_3GeSiClH_2$, $Cl_3GeSiH_3$, $HCl_2GeSiH_3$, $H_2ClGeSiH_3$, $HCl_2GeSiCl_2H$ and $H_2ClGeSiClH_2$. Other silicon germanium sources are derived by the replacement of at least one H-atom and/or at least one Cl-atom with another halogen, such as fluorine. Therefore, silicon germanium sources may have chemical formulas such as $F_3SiGeCl_3$, $F_3SiGeH_3$, $F_3GeSi_3$, $F_3GeSiH_3$, $H_3SiGeCl_3$, $H_3SiGeHCl_2$, $F_3SiGeCl_2H$, $F_3SiGeClH_2$, $HCl_2SiGeH_3$, $H_2ClSiGeF_3$, $FCl_2SiGeCl_2H$, $H_2ClSiGeClH_2$, $F_3GeSiCl_2H$, $F_3GeSiClH_2$ and $H_2FGeSiClH_2$. Other similarly halogenated silicon germanium sources enable the processes.

Silicon carbon sources may have formulas such as $H_3SiCH_3$, $Cl_3SiCCl_3$, $Cl_3SiCCl_2H$, $Cl_3SiCClH_2$, $Cl_3SiCH_3$, $HCl_2SiCH_3$, $H_2ClSiCH_3$, $HCl_2SiCCl_2H$, $H_2ClSiCClH_2$, $Cl_3CSiCl_2H$, $Cl_3CSiClH_2$, $Cl_3CSiH_3$, $HCl_2CSiH_3$, $H_2ClCSiH_3$, $HCl_2CSiCl_2H$ and $H_2ClCSiClH_2$. Other silicon carbon sources are derived by the replacement of at least one H-atom and/or at least one Cl-atom with another halogen, such as fluorine. Therefore, silicon carbon sources may have chemical formulas such as $Cl_3SiCF_2H$, $Cl_3SiCFH_2$, $F_3SiCH_3$, $FCl_2SiCH_3$, $H_2FSiCH_3$, $FCl_2SiCCl_2H$, $FH_2ClSiCClH_2$, $FCl_3CSiCl_2H$, $Cl_3CSiClHF$, $F_3CSiH_3$, $F_3CSiCl_3$, $H_3CSiF_3$, $Cl_3CSiF_3$, $FCl_2CSiH_3$, $H_2FCSiH_3$, $FCl_2CSiCl_2H$ and $H_2ClCSiFH_2$. Other similarly halogenated silicon carbon sources enable the processes.

Silicon compounds may be used to deposit a silicon motif (e.g., Si—R, where R is silicon, germanium or carbon) contained within the molecule. The hydrogens and/or halogens are ligands that are removed from the molecule as the silicon motif is reduced and deposited. The deposition forms a silicon-containing film during the procedure. The ligands may form an in-situ etchant from the liberated hydrogen and/or halogen. The in-situ etchants include H, $H_2$, HX, X, $X_2$ and XX', where X and X' are different, but both halogen, as well as other combinations of hydrogen and halogen molecules including radical or ionic species (e.g., .H or .X). Herein, the word halogen includes fluorine, chlorine, bromine, iodine, radicals thereof, ions thereof and combinations thereof.

In another aspect, embodiments of the invention relate to silicon compound comprising structures:

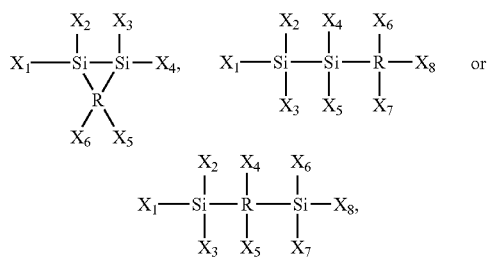

wherein $X_1$-$X_8$ are independently hydrogen or halogen, R is carbon, silicon or germanium and $X_1$-$X_8$ comprise at least one halogen. In some embodiments, the silicon-containing film is selected from the group consisting of silicon, silicon germanium, silicon carbon and silicon germanium carbon.

Other silicon compounds are used to deposit a silicon motif (e.g., Si—Si—R or Si—R—Si, where R is silicon, germanium or carbon) contained within the molecule. Silicon sources may have formulas such as $H_3SiSiH_2SiH_2Cl$, $H_3SiSiH_2SiHCl_2$, $H_3SiSiH_2SiCl_3$, $H_3SiSiHClSiH_2Cl$, $H_3SiSiHClSiHCl_2$, $H_3SiSiHClSiCl_3$, $H_3SiSiCl_2SiH_2Cl$, $H_3SiSiCl_2SiHCl_2$, $H_3SiSiCl_2SiCl_3$, $HCl_2SiSiH_2SiH_2Cl$, $HCl_2SiSiH_2SiHCl_2$, $Cl_3SiSiH_2SiCl_3$, $HCl_2SiSiCl_2SiH_2Cl$, $H_2ClSiSiHClSiHCl_2$, $Cl_3SiSiH_2SiCl_3$, $Cl_3SiSiHClSiCl_3$, $HCl_2SiSiCl_2SiHCl_2$ and $H_3SiSiCl_2SiH_3$. Other silicon sources are derived by the replacement of at least one H-atom and/or at least one Cl-atom with another halogen, such as fluorine. Therefore, silicon sources may have formulas such as $F_3SiSiH_2SiH_3$, $F_3SiSiH_2SiCl_3$, $H_3SiSiH_2SiH_2F$, $H_3SiSiH_2SiHF_2$, $H_3SiSiH_2SiF_3$, $H_3SiSiHFSiH_2Cl$, $F_3SiSiHClSiHF_2$, $H_3SiSiFHSiCl_3$, $H_3SiSiF_2SiH_2F$, $H_3SiSiCl_2SiFCl_2$, and $H_3SiSiF_2SiCl_3$. Other similarly halogenated silicon sources enable the processes. Furthermore, cyclic-trisilane and cyclic-halotrisilane are used within the scope of the invention.

Silicon germanium sources may have formulas such as $H_3SiSiH_2GeH_2Cl$, $H_3SiSiH_2GeH_3$, $H_3SiSiH_2GeHCl_2$, $H_3SiSiH_2GeCl_3$, $H_3SiSiHClGeH_2Cl$, $H_3SiSiHClGeHCl_2$, $H_3SiGeHClSiCl_3$, $H_3SiGeCl_2SiH_2Cl$, $H_3SiGeCl_2SiHCl_2$, $H_3SiGeCl_2SiCl_3$, $HCl_2SiGeH_2SiH_2Cl$, $HCl_2SiSiH_2GeHCl_2$, $Cl_3SiSiH_2GeCl_3$, $HCl_2SiGeCl_2SiH_2Cl$, $H_2ClSiGeHClSiHCl_2$, $Cl_3SiGeH_2SiCl_3$, $Cl_3SiSiHClGeCl_3$, $HCl_2SiGeCl_2SiH_3$ and $H_3GeSiCl_2SiH_3$. Other silicon germanium sources are derived by the replacement of at least one H-atom and/or at least one Cl-atom with another halogen, such as fluorine. Therefore, silicon germanium sources have formulas such as $F_3SiSiH_2GeH_3$, $F_3SiSiH_2GeCl_3$, $F_3GeSiH_2SiH_3$, $F_3GeSiH_2SiCl_3$, $F_3SiGeH_2SiH_3$, $F_3SiGeH_2SiCl_3$, $F_3SiSiH_2GeCl_2H$, $H_3SiSiF_2GeH_2Cl$, $F_3SiGeH_2GeHCl_2$, $H_3SiSiF_2GeCl_3$, $H_3SiSiCl_2GeH_2Cl$, $H_3SiSiHClGeHF_2$, $H_3SiGeH_2SiCl_3$, $H_3SiGeCl_2SiH_2Cl$, $F_3SiGeCl_2SiHCl_2$, $H_3SiGeF_2SiCl_3$. Other similarly halogenated silicon germanium sources enable the processes. Furthermore, cyclic germaniumsilanes and cyclic-halogermaniumsilanes are used within the scope of the invention.

Silicon carbon sources may have formulas such as $H_3SiSiH_2CH_2Cl$, $H_3SiSiH_2CHCl_2$, $H_3SiSiH_2CCl_3$, $H_3SiSiHClCH_2Cl$, $H_3SiSiHClCHCl_2$, $H_3SiCHClSiCl_3$, $H_3SiCCl_2SiH_2Cl$, $H_3SiCCl_2SiHCl_2$, $H_3SiCCl_2SiCl_3$, $HCl_2SiCH_2SiH_2Cl$, $HCl_2SiSiH_2CHCl_2$, $Cl_3SiSiH_2CCl_3$, $HCl_2SiCCl_2SiH_2Cl$, $H_2ClSiCHClSiHCl_2$, $Cl_3SiCH_2SiCl_3$, $Cl_3SiSiHClCCl_3$, $HCl_2SiCCl_2SiH_3$ and $H_3CSiCl_2SiH_3$. Other silicon carbon sources are derived by the replacement of at least one H-atom and/or at least one Cl-atom with another halogen, such as fluorine. Therefore, silicon carbon sources have formulas such as $F_3SiSiH_2CH_3$, $F_3SiSiH_2CCl_3$, $F_3CSiH_2SiH_3$, $F_3CSiH_2SiCl_3$, $F_3SiCH_2SiH_3$, $F_3SiCH_2SiCl_3$, $F_3SiSiH_2CCl_2H$, $H_3SiSiF_2CH_2Cl$, $F_3SiSiH_2CHCl_2$, $H_3SiSiF_2CCl_3$, $H_3SiSiHFCH_2Cl$, $H_3SiSiHClCHF_2$, $H_3SiCHFSiCl_3$, $H_3SiCCl_2SiH_2F$, $F_3SiCCl_2SiHCl_2$, $H_3SiCF_2SiCl_3$. Other similarly halogenated silicon carbon sources enable the processes. Furthermore, cyclic-carbosilanes and cyclic-halocarbosilanes are used within the scope of the invention.

In another aspect, embodiments of the invention relate to silicon compounds, compounds 1-8, having the following representative structures:

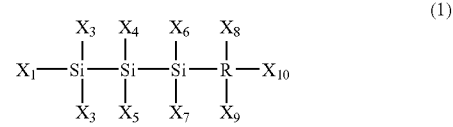

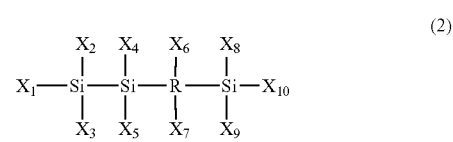

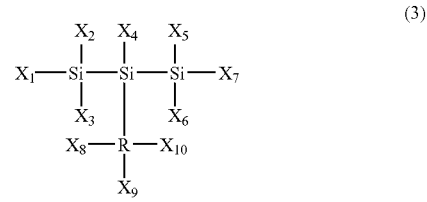

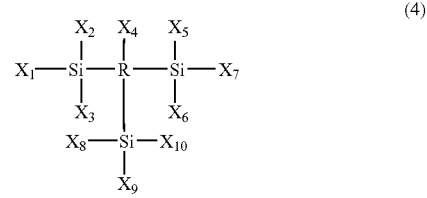

-continued
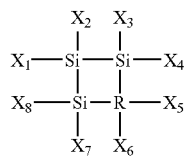 (5)
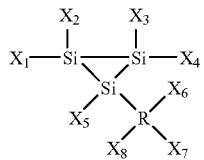 (6)
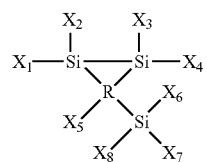 (7)
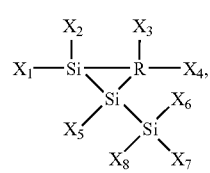 (8)
where $X_1$-$X_{10}$ are independently hydrogen or halogen, such as fluorine, chlorine, bromine or iodine and R is carbon, silicon or germanium.
In another aspect, embodiments of the invention relate to silicon compounds, compounds 9-32, having the following representative structures:
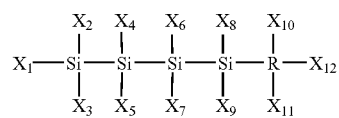 (9)
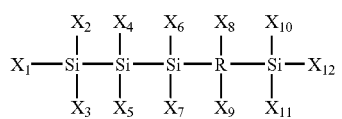 (10)
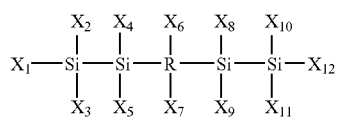 (11)
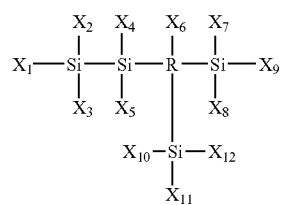 (12)
-continued
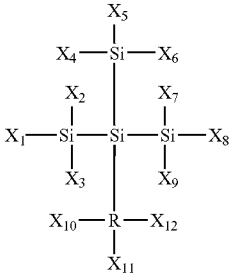 (13)
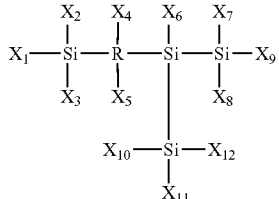 (14)
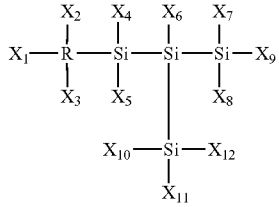 (15)
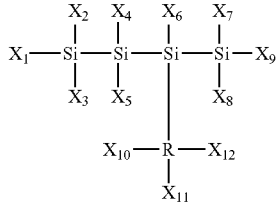 (16)
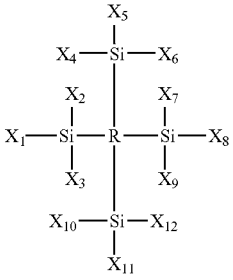 (17)
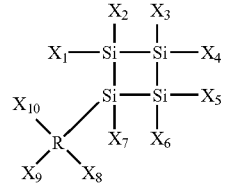 (18)
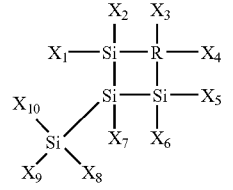 (19)

-continued

(20) 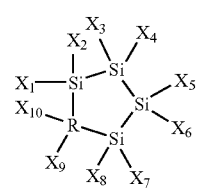

(21) 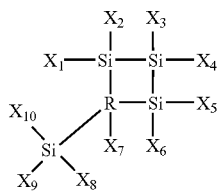

(22) 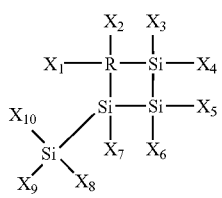

(23) 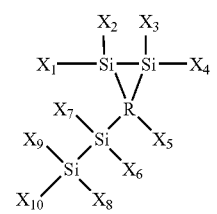

(24) 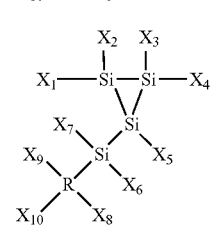

(25) 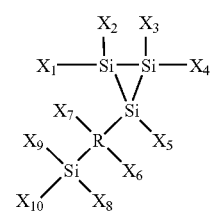

(26) 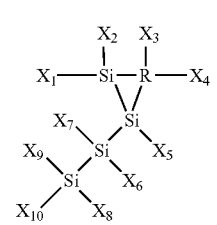

(27) 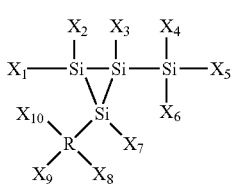

-continued

(28) 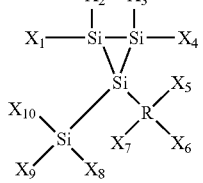

(29) 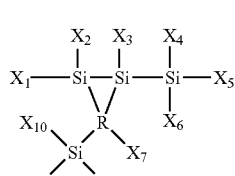

(30) 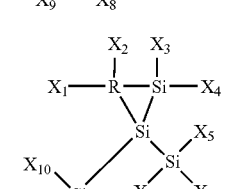

(31) 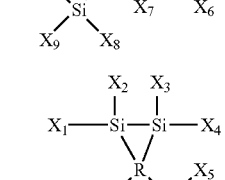

(32) 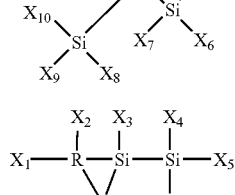

where $X_1$-$X_{12}$ are independently hydrogen or halogen, such as fluorine, chlorine, bromine or iodine and R is carbon, silicon or germanium. The structures of compounds 1-32 are representative and do not imply a particular isomer. Herein, any elemental name or chemical symbol anticipates the use of the respective elemental isotopes, such as the use of hydrogen ($^1$H or H) also includes the use of deuterium ($^2$H or D) and tritium ($^3$H or T).

Therefore, silicon compounds may be used to deposit a silicon motif (e.g., $Si_3R$ or $Si_4R$, where R is silicon, germanium or carbon) contained within the molecule. The silicon motif of compounds 1-8 is represented by $Si_3R$ and the silicon motif of compounds 9-32 is represented by $Si_4R$. The hydrogens and/or halogens are ligands that are removed from the molecule as the silicon motif is reduced and deposited. The deposition forms a silicon-containing film during the deposition process.

Silicon sources may include compounds with the formulas $Si_4X_8$, $Si_4X_{10}$, $Si_5X_{10}$ and $Si_5X_{12}$, where X is independently hydrogen or halogen. Silicon sources containing hydrogen and/or chlorine may include compounds with the formulas $Si_4H_{8-n}Cl_n$, $Si_4H_{10-m}Cl_m$, $Si_5H_{10-p}Cl_p$ and $Si_5H_{12-q}Cl_q$, where n=1-8, m=1-10, p=1-10 and q=1-12. Silicon sources may include $Si_4H_9Cl$, $Si_4H_8Cl_2$, $Si_4H_7Cl_3$, $Si_4H_6Cl_4 Si_4H_5Cl_5$, $Si_4H_4Cl_6$, $Si_4H_3Cl_7$, $Si_4H_2Cl_8$, $Si_4HCl_9$, $Si_4Cl_{10}$, $Si_5H_{11}Cl$, $Si_5H_{10}Cl_2$, $Si_5H_9Cl_3$, $Si_5H_8Cl_4$, $Si_5H_7Cl_5$, $Si_5H_6Cl_6$, $Si_5H_5Cl_7$, $Si_5H_4Cl_8$, $Si_5H_3Cl_9$, $Si_5H_2Cl_{10}$, $Si_5HCl_{11}$ and $Si_5Cl_{12}$. Other silicon sources are derived by the replacement of at least one Cl-atom with another halogen, such as fluorine, bromine or iodine and enable the processes. In one example, isotetrasilane, $(SiH_3)_3SiH$, is a silicon source compound. In another example, neopentasilane, $(SiH_3)_4Si$, is a silicon source compound. Furthermore, cyclic-tetrasilane, cyclic-halotetrasilane, cyclic-pentasilane and cyclic-halopentasilane are used within the scope of the invention.

Silicon germanium sources may include compounds with the formulas $Si_3GeX_8$, $Si_3GeX_{10}$, $Si_4GeX_{10}$ and $Si_4GeX_{12}$, where X is independently hydrogen or halogen. Silicon germanium sources containing hydrogen and/or chlorine may include compounds with the formulas $Si_3GeH_{8-n}Cl_n$, $Si_3GeH_{10-m}Cl_m$, $Si_4GeH_{10-p}Cl_p$ and $Si_4GeH_{12-q}Cl_q$, where n=1-8, m=1-10, p=1-10 and q=1-12. Silicon germanium sources may include $Si_3GeHgCl$, $Si_3GeH_8Cl_2$, $Si_3GeH_7Cl_3$, $Si_3GeH_6Cl_4$, $Si_3GeH_5Cl_5$, $Si_3GeH_4Cl_6$, $Si_3GeH_3Cl_7$, $Si_3GeH_2Cl_8$, $Si_3GeHCl_9$, $Si_3GeC_{10}$, $Si_4GeH_{11}Cl$, $Si_4GeH_{10}Cl_2$, $Si_4GeH_9Cl_3$, $Si_4GeH_8Cl_4$, $Si_4GeH_7Cl_5$, $Si_4GeH_6Cl_6$, $Si_4GeH_5Cl_7$, $Si_4GeH_4Cl_8$, $Si_4GeH_3Cl_9$, $Si_4GeH_2Cl_{10}$, $Si_4GeHCl_{11}$ and $Si_4GeCl_{12}$. Other silicon germanium sources are derived by the replacement of at least one Cl-atom with another halogen, such as fluorine, bromine or iodine and enable the processes. Furthermore, cyclic germaniumsilanes and cyclic-halogermaniumsilanes are used within the scope of the invention.

Silicon carbon sources may include compounds with the formulas $Si_3CX_8$, $Si_3CX_{10}$, $Si_4CX_{10}$ and $Si_4CX_{12}$, where X is independently hydrogen or halogen. Silicon carbon sources containing hydrogen and/or chlorine may include compounds with the formulas $Si_3CH_{8-n}Cl_n$, $Si_3CH_{10-m}Cl_m$, $Si_4CH_{10-p}Cl_p$ and $Si_4CH_{12-q}Cl_q$, where n=1-8, m=1-10, p=1-10 and q=1-12. Silicon carbon sources may include $Si_3CH_gCl$, $Si_3CH_8Cl_2$, $Si_3CH_7Cl_3$, $Si_3CH_6Cl_4$, $Si_3CH_5Cl_5$, $Si_3CH_4Cl_6$, $Si_3CH_3Cl_7$, $Si_3CH_2Cl_8 Si_3CHCl_9$, $Si_3CCl_{10}$, $Si_4CH_{11}Cl$, $Si_4CH_{10}Cl_2$, $Si_4CH_9Cl_3$, $Si_4CH_8Cl_4$, $Si_4CH_7Cl_5$, $Si_4CH_6Cl_6$, $Si_4CH_5Cl_7$, $Si_4CH_4Cl_8$, $Si_4CH_3Cl_9$, $Si_4CH_2Cl_{10}$, $Si_4CHCl_{11}$ and $SiCCl_{12}$. Other silicon carbon sources are derived by the replacement of at least one Cl-atom with another halogen, such as fluorine, bromine or iodine and enable the processes. Furthermore, cyclic carbonsilanes and cyclic-halocarbonsilanes are used within the scope of the invention.

Many of the silicon compounds are in the gaseous or liquid state at ambient pressure and temperature. However, during a deposition process, the silicon compounds may be in solid, liquid, gas or plasma state of matter, as well as radical or ionic. In general, the silicon compounds may be delivered to the substrate surface by a carrier gas. Carrier or purge gases may include $N_2$, $H_2$, Ar, He, forming gas and combinations thereof.

Silicon compounds may be used solely or in combination with compounds, including other silicon compounds, to deposit silicon-containing films with a variety of compositions. In one example, a silicon compound, such as $Cl_3SiSiH_2SiH_2SiH_3$, is used to etch the substrate surface, as well as to epitaxially grow a crystalline silicon film on the substrate. In another example, the substrate surface may need a different etchant than in the previous example. Therefore, $Cl_3SiSiH_2SiCl_2SiH_2F$ is used in the etching process, while $H_2ClSiSiH_2SiH_2SiH_3$ is used in the deposition process. In another example, a silicon germanium source, such as $H_3SiSiH_2SiH_2GeHCl_2$, is used to continue the deposition process and to grow a silicon germanium film on the silicon film.

In another embodiment, the $RF_3$ fragment, where R=Si, Ge or C, can be incorporated into the molecule. The $RF_3$ is thermodynamically stable due to the strong R—F bond. A molecule, such as $F_3CSiH_2SiH_3SiH_3$, decomposes to deposit silicon-containing films, while the $CF_3$ fragment is generated as part of a volatile product. A silicon compound with the $RF_3$ fragment can have favorable properties, such as volatility (vapor pressure and boiling point).

Silicon compounds are utilized within embodiments of the processes to deposit silicon-containing films used for Bipolar (base, emitter, collector, emitter contact), BiCMOS (base, emitter, collector, emitter contact) and CMOS (channel, source/drain, source/drain extension, elevated source/drain, substrate, strained silicon, silicon on insulator, isolation, contact plug). Other embodiments of processes teach the growth of silicon-containing films that can be used as gate, base contact, collector contact, emitter contact, elevated source/drain and other uses.

Embodiments of the invention teach processes to grow selective silicon films or blanket silicon films. Selective silicon film growth generally is conducted when the substrate or surface includes more than one material, such as a crystalline silicon surface having oxide or nitride features. Usually, these features are dielectric material. Selective epitaxial growth to the crystalline, silicon surface is achieved while the feature is left bare, generally, with the utilization of an etchant (e.g., HCl). The etchant removes amorphous silicon or polysilicon growth from features quicker than the etchant removes crystalline silicon growth from the substrate, thus selective epitaxial growth is achieved. In some embodiments, selective epitaxial growth of the silicon-containing film is accomplished with the use of no etchants. During blanket silicon epitaxy, a film grows across the whole substrate regardless of particular surface features and compositions.

Embodiments of the invention teach processes to grow selective silicon films or blanket silicon films. Selective silicon film growth generally is conducted when the substrate or surface includes more than one material, such as a crystalline silicon surface having oxide or nitride features. Usually, these features are dielectric material. Selective epitaxial growth to the crystalline, silicon surface is achieved while the feature is left bare, generally, with the utilization of an etchant (e.g., HCl). The etchant removes amorphous silicon or polysilicon growth from features quicker than the etchant removes crystalline silicon growth from the substrate, thus selective epitaxial growth is achieved. In some embodiments, selective epitaxial growth of the silicon-containing film is accomplished with the use of no etchants. During blanket silicon epitaxy, a film grows across the whole substrate regardless of particular surface features and compositions.

Embodiments of the invention may use processes with an etchant source and a silicon source incorporated into the silicon compound. The deposition processes form silicon-containing films and liberate ligands from the silicon compounds. The ligands, hydrogen and/or halogen, are in-situ etchants. The in-situ etchants include H. $H_2$, HX, X, $X_2$ and XX', where X is a halogen and X' is a different halogen than X, as well as any other combinations of hydrogen and halogen molecules including radical or ionic species. However, supplemental etchants can also be used with the silicon compounds and are demonstrated in various embodiments of the invention. Supplemental etchants can include: $CHF_3$, $CF_4$, $C_4F_8$, $CH_2F_2$, $ClF_3$, $Cl_2$, $F_2$, $Br_2$, $NF_3$, HCl, HF, HBr, $XeF_2$, $NH_4F$, $(NH_4)(HF_2)$ and $SF_6$. For example, $H_3SiSiH_2SiH_2SiCl_2H$ and HCl are used during the growth of a silicon-containing film.

In some processes, silicon compounds are introduced to the heated (e.g., 500° C.) surface of a substrate and the silicon motif is deposited as the silicon-containing film. The liberated ligands of the silicon compounds are converted to an in-situ etchant. The in-situ etchants support in the growth of selective silicon epitaxy by removing amorphous silicon or polysilicon from substrate features (e.g., oxides or nitrides) at a faster rate than removing crystalline silicon from the surface. Hence, crystalline silicon grows about the substrate features.

Reducing agents may be used in various embodiments of the invention to transfer electrons between compounds. Generally, silicon compounds are reduced to elemental films during deposition, while the ligands (e.g., hydrogen or halogen) are detached from the silicon motif. Reducing agents may include: mono- and diatomic hydrogen, borane, diborane, alkyboranes (e.g., $Me_3B$ or $Et_3B$), metals and organometallic compounds among others. In one example, a silicon-containing film is deposited by alternating pulses of $F_3SiSiH_2SiH_2CH_3$ with atomic hydrogen.

Embodiments of the processes deposit silicon-containing materials on many substrates and surfaces. Substrates on which embodiments of the invention can be useful include, but are not limited to semiconductor wafers, such as crystalline silicon (e.g., Si<100> and Si<111>), silicon on substrate, silicon oxide, silicon germanium, doped or undoped wafers and patterned or non-patterned wafers. Surfaces include wafers, films, layers and materials with dielectric, conductive and barrier properties and include polysilicon, silicon on insulators (SOI), strained and unstrained lattices. Some substrate surface may include glass, such as activated (e.g., Pd) glass substrates. Pretreatment of surfaces includes polishing, etching, activating, reduction, oxidation, hydroxylation, annealing and baking. In one embodiment, wafers are dipped into a 1% HF solution, dried and baked in a hydrogen atmosphere at 800° C.

Embodiments of the processes may be used to grow silicon-containing films with many compositions and properties, including crystalline, amorphous or polysilicon films. Silicon-containing film is the term used herein to describe a variety of product compositions formed by embodiments of the invention. Some silicon-containing films include crystalline or pure silicon, silicon germanium, silicon carbon and silicon germanium carbon. Other silicon-containing films include epi-SiGe, epi-SiGeC, epi-SiC, poly-SiGe, poly-SiGeC, poly-SiC, α-Si, silicon nitride, silicon oxynitride, silicon oxide and metal silicates (e.g., where metals include titanium, zirconium and hafnium). Silicon-containing films include strained or unstrained layers.

Silicon-containing films may include a germanium concentration within the range from about 0 atomic percent to about 95 atomic percent. In other aspects, a germanium concentration is within the range from about 1 atomic percent to about 30 atomic percent. Silicon-containing films may include a carbon concentration within the range from about 0 atomic percent to about 5 atomic percent. In other aspects, a carbon concentration is within the range from about 200 ppm to about 2 atomic percent.

Chlorine and hydrogen incorporation into silicon films has plagued the prior art by the use of lower silanes, lower halosilanes or hexachlorodisilane. Some processes of the invention deposit silicon-containing film that can include impurities, such as hydrogen, halogen and other elements. However, the halogen impurities (e.g., F) occur within the deposited silicon-containing film and are acceptable at less than about $3 \times 10^{16}$ atoms/cm$^3$. Generally, embodiments of the invention may grow silicon-containing films as thick as a single atomic layer, about 2.5 Å, and as thick as about 120 μm, preferably with a thickness in the range from about 2.5 Å to about 10 μm. Various embodiments of the invention teach growing films with a thickness in the range from about 10 Å to about 100 Å, from about 100 Å to about 1,000 Å, from about 1,000 Å to about 1 μm, from about 1 μm to about 4 μm, from about 4 μm to about 50 μm and from about 50 μm to about 120 μm. In other embodiments, film thickness is in the range from about 2.5 Å to about 120 μm, from about 2.5 Å to about 4 μm and from about 2.5 Å to about 100 Å.

The silicon-containing films made by processes of the invention can be doped. In one embodiment, a selective epitaxy silicon layer is doped P type, such as by using diborane to add boron at a concentration in the range from about $10^{15}$ atoms/cm$^3$ to about $10^{20}$ atoms/cm$^3$. In another embodiment, a polysilicon layer is doped N$^+$ type, such as by ion implanting of phosphorus to a concentration in the range from about $10^{19}$ atoms/cm$^3$ to about $10^{21}$ atoms/cm$^3$. In another embodiment, a selective epitaxy silicon layer is doped N$^-$ type, such as by diffusion of arsenic or phosphorus to a concentration in the range from about $10^{15}$ atoms/cm$^3$ to about $10^{19}$ atoms/cm$^3$.

The silicon-containing films of germanium and/or carbon are produced by various processes of the invention and can have consistent, sporadic or graded elemental concentrations. Graded silicon germanium films are disclosed in commonly assigned U.S. Ser. No. 09/866,172, published as U.S. Pub. No. 2002-0174826, and issued as U.S. Pat. No. 6,770,134 and commonly assigned U.S. Ser. No. 10/014,466, published as U.S. Pub. No. 2002-0174827, and issued as U.S. Pat. No. 6,905,542, which are incorporated herein by reference in entirety for the purpose of describing methods of depositing graded silicon-containing films. In one embodiment, silicon germanium sources (e.g., $Cl_3SiSiH_2SiCl_2GeH_3$) are used to deposit silicon germanium containing films. In another embodiment, silicon sources (e.g., $Cl_3SiSiH_2SiH_2SiH_3$) and alternative germanium sources (e.g., $GeH_4$ or $Ge_2H_6$) are used to deposit silicon germanium containing films. In this embodiment, the ratio of silicon source and germanium source can be varied in order to provide control of the elemental concentrations while growing graded films.

In another embodiment, silicon carbon sources (e.g., $Cl_3SiSiH_2SiH_2CH_3$) are used to deposit silicon carbon containing films. In another embodiment, silicon sources (e.g., $Cl_3SiSiH_2SiH_2SiH_3$) and alternative carbon sources (e.g., $C_2H_4$) are used to deposit silicon carbon containing films. The ratio of silicon source and carbon source can be varied in order to provide control of the elemental concentration while growing homogenous or graded films.

Furthermore, in another embodiment, silicon carbon sources (e.g., $Cl_3SiSiH_2SiH_2GeH_3$) and alternative germanium sources (e.g., $GeH_4$ or $Ge_2H_6$) are used to deposit silicon germanium carbon containing films. The amounts of silicon carbon source and germanium source can be varied to provide control of the elemental concentrations while growing graded films. In another embodiment, silicon germanium sources (e.g., $Cl_3SiSiH_2SiH_2GeH_3$) and alternative carbon sources (e.g., $C_2H_4$) are used to deposit a silicon germanium carbon containing films. The ratio of silicon germanium source and carbon source can be varied to provide control of the elemental concentrations while growing graded films. In other embodiments, silicon germanium carbon containing films are deposited by combining mixtures of silicon sources with silicon germanium sources and/or alternative germanium sources and/or silicon carbon sources and/or alternative carbon sources. Therefore, any silicon compound, silicon source, silicon germanium source, silicon carbon source, alternative silicon source, alternative germanium source and alternative carbon source can be used solely or in combination to deposit silicon-containing films.

Alternative silicon sources may include silanes (e.g., $SiH_4$) and halogenated silanes (e.g., $H_{4-n}SiX_n$, where X is independently F, Cl, Br or I and n=1-4), for example, $ClSiH_3$, $Cl_2SiH_2$, $Cl_3SiH$ and $Cl_4Si$. Alternative germanium sources may include germanes (e.g., $GeH_4$, $Ge_2H_6$, $Ge_3H_8$ or $Ge_4H_{10}$) and halogenated germanes (e.g., $H_{4-n}GeX_n$, where X is independently F, Cl, Br or I and n=1-4). Alternative carbon sources may include alkanes (e.g., $CH_4$, $C_2H_6$, $C_3H_8$, $C_4H_{10}$), halogenated alkanes (e.g., $H_{4-n}CX_n$, where X independently F, Cl, Br or I and n=1-4), alkenes (e.g., $C_2H_4$) and alkynes (e.g., $C_2H_2$).

Silicon compounds may be used in various deposition processes of the invention with temperatures in a range from about ambient temperature (e.g., 23° C.) to about 1,200° C. Multiple temperature regions may be controlled throughout the deposition process, such as the process chamber and a delivery line in fluid communication with a precursor source and the process chamber. For example, deposition processes may be conducted with a process chamber at a temperature within the range from about 100° C. to about 1,000° C. while a delivery line has a temperature within the range from about ambient to about 250° C. In other embodiments, the process temperature is less than about 700° C. and is often less than about 500° C. In some embodiments, supplemental reducing agents may be used while depositing a silicon-containing film. In other embodiments, a silicon0containing film is deposited by pyrolysis of the silicon compounds.

In processes of the invention, silicon-containing films are grown by chemical vapor deposition (CVD) processes and include ALE and atomic layer deposition (ALD). Chemical vapor deposition includes the use of many techniques, such as plasma-assisted CVD (PA-CVD), thermal-induced CVD, atomic layer CVD (ALCVD), organometallic or metalorganic CVD (OMCVD or MOCVD), laser-assisted CVD (LA-CVD), ultraviolet CVD (UV-CVD), hot-wire (HWCVD), reduced-pressure CVD (RP-CVD), ultra-high vacuum CVD (UHV-CVD) and others.

In some embodiments of the invention, silicon-containing film may be deposited by ALD. For example, an ALD process is conducted by sequential cycles that include: a pulse of a silicon compound, adsorption of the silicon compound on the substrate or surface, a purge of the reaction chamber, a reduction of the adsorbed silicon compound and a purge of the reaction chamber. Alternatively, when the reduction step includes a reductant pulse, such as atomic hydrogen, the cycle includes: a pulse of a reductant compound, adsorption of the reductant compound on the substrate or surface, a purge of the reaction chamber, a pulse of the silicon compound, reduction of the silicon compound and a purge of the reaction chamber.

The time duration for each silicon compound pulse, the time duration for each reductant pulse and the duration of the purge gas between pulses of the reactants are variable and depend on the volume capacity of a deposition chamber employed, as well as a vacuum system coupled thereto. For example, (1) a lower gas pressure in the chamber will require a longer pulse time; (2) a lower gas flow rate will require a longer time for chamber pressure to rise and stabilize requiring a longer pulse time; and (3) a large-volume chamber will take longer to fill, longer for chamber pressure to stabilize thus requiring a longer pulse time. Similarly, time between each pulse is also variable and depends on volume capacity of the process chamber as well as the vacuum system coupled thereto. In general, the time duration of the silicon compound pulse or the reductant pulse should be long enough for adsorption of the compound. In one example, the silicon compound pulse may still be in the chamber when the reductant pulse enters. In general, the duration of the purge gas should be long enough to prevent the pulses of the silicon compound and the reductant compound from mixing in the reaction zone.

Generally, a pulse time of about 1.0 second or less for a silicon compound and a pulse time of about 1.0 second or less for a reductant are typically sufficient to adsorb alternating amounts of reactants on a substrate or surface. A time of about 1.0 second or less between pulses of the silicon compound and the reductant is typically sufficient for the purge gas to prevent the pulses of the silicon compound and the reductant from mixing in the reaction zone. Of course, a longer pulse time of the reactants may be used to ensure adsorption of the silicon compound and the reductant and a longer time between pulses of the reactants may be used to ensure removal of the reaction by-products.

The processes of the invention may be carried out in equipment known in the art of ALE, CVD and ALD. The apparatus brings the sources into contact with a substrate on which the silicon-containing films are grown. The processes may operate at a range of pressures from about 1 mTorr to about 2,300 Torr depending on specific deposition process and hardware. For example, a silicon-containing film may be deposited by a CVD process with a pressure in the range from about 0.1 Torr to about 760 Torr. In another example, a silicon-containing film may be deposited by an ALD process with a pressure in the range from about 760 Torr to about 1,500 Torr. Hardware that may be used to deposit silicon-containing films includes the Epi CENTURA® system and the POLYGEN™ system available from Applied Materials, Inc., located in Santa Clara, Calif. An ALD apparatus that may be used to deposit silicon-containing films is disclosed in commonly assigned U.S. Ser. No. 10/032,284, published as U.S. Pub. No. 2003-0079686, and issued as U.S. Pat. No. 6,916,398, which is incorporated herein by reference in entirety for the purpose of describing the apparatus. Other apparatuses include batch, high-temperature furnaces, as known in the art.

Another embodiment of the invention teaches methods to synthesize silicon compounds comprising $SiRX_6$, $Si_2RX_6$, $Si_2RX_8$, compounds 1-8 and compounds 9-32, wherein X is independently hydrogen or halogen, R is carbon, silicon or germanium. Disproportionation reactions of non-halogenated, higher silanes are known in the art, such as U.S. Pat. No. 6,027,705, which is incorporated herein by reference in entirety for the purpose of describing the syntheses of silicon compounds. Silanes, halosilanes, germanes, halogermanes, alkyls and haloalkyls may be used as starting materials to form silicon compounds. In some embodiments, silicon compounds may be used as starting materials for other silicon compounds. Starting materials may be made into radical compounds by a variety of methods and include thermal decomposition or plasma excitation. Starting material radicals combine to form silicon compounds. In one example, $.SiH_2SiH_3$ and $.SiCl_2SiCl_3$ are respectively made from disilane and hexachlorodisilane and are combined to form $H_3SiSiH_2SiCl_2SiCl_3$. In another example, $.SiH_2SiH_2SiH_3$ and $.GeCl_3$ are respectively made from trisilane and tetrachlorogermane and are combined to form $H_3SiSiH_2SiH_2GeCl_3$. In another example, $.GeH_3$ and $.SiCl_2SiCl_2SiCl_3$ are respectively made from germane and octachlorotrisilane and are combined to form $H_3GeSiCl_2SiCl_2SiCl_3$. In another example, $.CF_3$ and $.SiH_2SiH_2SiH_3$ are respectively made from tetrafluoromethane and trisilane and are combined to form $F_3CSiH_2SiH_2SiH_3$. In another example, .SiH$_2$SiH$_2$SiH$_3$ and .SiCl$_2$SiCl$_3$ are respectively made from trisilane and hexachlorodisilane and are combined to form $H_3SiSiH_2SiH_2SiCl_2SiCl_3$. In another example, .Si H$_2$SiH$_2$SiH$_2$SiH$_3$ and .GeCl$_3$ are respectively made from tetrasilane and tetrachlorogermane and are combined to form $H_3SiSiH_2SiH_2SiH_2GeCl_3$. In another example, .GeH$_3$ and .Si Cl$_2$SiCl$_2$SiCl$_2$SiCl$_3$ are respectively made from germane and decachlorotetrasilane and are combined to form $H_3GeSiCl_2SiCl_2SiCl_2SiCl_3$. In another example, .CF$_3$ and .Si H$_2$SiH$_2$SiH$_3$ are respectively made from tetrafluoromethane and tetrasilane and are combined to form $F_3CSiH_2SiH_2SiH_2SiH_3$.

THEORETICAL EXPERIMENTS 1-17
INCLUDING SILICON COMPOUNDS SiRX$_6$

Example 1

Monocrystalline Silicon by Selective CVD

A substrate, Si<100>, was employed to investigate selective, monocrystalline film growth by CVD. A silicon oxide feature existed on the surface of the wafer. The wafer was prepared by subjecting to a 0.5% HF dip for 30 seconds followed by baking at 750° C. for 60 seconds. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 30 sccm of Cl$_3$SiSiH$_3$, was delivered to the chamber at 10 Torr and 750° C. The substrate was maintained at 750° C. Deposition was carried out for 3 minutes to form a 400 Å epitaxial layer on the silicon surface, but no epitaxial growth occurred on the silicon dioxide surface.

Example 2

Monocrystalline Silicon by Blanket CVD

A substrate, Si<100>, was employed to investigate blanket, monocrystalline film growth by CVD. A silicon oxide feature existed on the surface of the wafer. The wafer was prepared by subjecting to a 0.5% HF dip for 30 seconds followed by baking at 750° C. for 60 seconds. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 50 sccm of Cl$_3$SiSiH$_3$, was added to the chamber at 100 Torr and 650° C. The substrate was maintained at 650° C. Deposition was carried out for 4 minutes to form a 1,600 Å epitaxial layer.

Example 3

Polysilicon by CVD

The substrate was prepared as in Example 2. The wafer was loaded into the deposition chamber (POLYGEN™ chamber) and subjected to a hydrogen purge for 2 minutes. A flow of carrier gas, hydrogen, was directed towards the substrate and the source compounds were added to the carrier flow. The silicon compound, 100 sccm of HF$_2$SiSiClH$_2$, was added to the chamber at 80 Torr and 550° C. The substrate was maintained at 550° C. Deposition was carried out for 3 minutes to form a 1,200 Å layer.

Example 4

Amorphous Silicon by CVD

A silicon dioxide layered wafer was loaded into the deposition chamber (Epi CENTURA® chamber) and subjected to a hydrogen purge for 1 minute. A flow of carrier gas, hydrogen, was directed towards the substrate and the source compounds were added to the carrier flow. The silicon compound, 200 sccm of HCl$_2$SiSiH$_3$, was added to the chamber at 200 Torr and 40° C. The substrate was maintained at 40° C. Deposition was carried out for 3 minutes to form a 200 Å layer.

Example 5

Silicon Germanium by CVD

The substrate was prepared as in Example 2. The wafer was loaded into the deposition chamber (Epi CENTURA® chamber) and subjected to a hydrogen purge for 1 minute. A flow of carrier gas, hydrogen, was directed towards the substrate and the source compounds were added to the carrier flow. The silicon compound, 10 sccm HCl$_2$SiGeH$_3$, was added to the chamber at 100 Torr and 650° C. The substrate was maintained at 650° C. Deposition was carried out for 5 minutes to form a 600 Å epitaxial layer.

Example 6

Silicon Carbon by CVD

The substrate was prepared as in Example 2. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of HCl$_2$CSiH$_3$, was added to the chamber at 100 Torr and 500° C. The substrate was maintained at 500° C. Deposition was carried out for 15 minutes to form a 1,400 Å epitaxial layer.

Example 7

Silicon Germanium Carbon by CVD

The substrate was prepared as in Example 2. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of HCl$_2$SiGeH$_3$, was added to the chamber at 100 Torr and 550° C. The silicon compound, H$_3$CSiH$_3$, was also added to the chamber at 2 sccm. The substrate was maintained at 550° C. Deposition was carried out for 10 minutes to form a 2,100 Å epitaxial layer.

Example 8

Doped Silicon CVD

The substrate was prepared as in Example 2. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 100 sccm of Cl$_3$SiSiH$_3$, was added to the chamber at 100 Torr and 750° C. The dopant compound, 1 sccm of 1000 ppm $B_2H_6$ in $H_2$, was also added to the chamber. The substrate was maintained at 750° C. Deposition was carried out for 3 minutes to form a 600 Å epitaxial doped layer.

Example 9

Graded Silicon Germanium by CVD

The substrate was prepared as in Example 2. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 50 sccm of $HCl_2SiSiH_3$, was added to the chamber at 10 Torr and 650° C. A decreasing flow from 225 sccm down to 5 sccm of the silicon compound, $HCl_2SiGeH_3$, was also added to the chamber during the deposition step. The flow rate was changed non-linearly in respect to time to produce a linearly graded final germanium content in the deposited film. The substrate was maintained at 550° C. Deposition was carried out for 5 minutes to form a 1,200 Å epitaxial layer.

Example 10

Graded Silicon Germanium Carbon by CVD

The substrate was prepared as in Example 2. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 100 sccm of $HCl_2SiCH_3$, was added to the chamber at 10 Torr and 650° C. Also, 10 sccm of 5% $H_3CSiH_3$ was added to the chamber. A decreasing flow from 350 sccm down to 5 sccm of the silicon compound, $HCl_2SiGeH_3$, was also added to the chamber during the deposition step. The flow rate was changed non-linearly to produce a linearly graded final germanium content in the deposited film. The substrate was maintained at 550° C. Deposition was carried out for 5 minutes to form a 1,300 Å epitaxial layer.

Example 11

Monocrystalline Selective Silicon by CVD with use of HCl:

The substrate was prepared as in Example 1. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2SiSiH_3$, was added to the chamber at 10 Torr and 600° C. A 5 sccm flow of hydrogen chloride was also delivered to the chamber. The substrate was maintained at 600° C. Deposition was carried out for 8 minutes to form a 500 Å epitaxial layer on the silicon surface, but no epitaxial growth occurred on the silicon dioxide surface.

Example 12

Graded silicon germanium by ALD

The substrate was prepared as in Example 2. The wafer was loaded into the deposition chamber and subjected to a hydrogen purge for 10 minutes. A flow of carrier gas, argon, was directed towards the substrate and the source compounds were pulsed into this flow. The H-atoms are generated via a tungsten hot-wire. ALD cycle A included: $HCl_2SiSiH_3$ (0.8 s), purge (1.0 s), H-atoms (1.2 s), purge (1.0 s). ALD cycle B included: $HCl_2SiGeH_3$ (0.8 s), purge (1.0 s), H-atoms (1.2 s), purge (1.0 s). A graded film is grown by running a sequence of cycles such as: 10A, 1B, 5A, 1B, 1A, 1B, 1A , 5B, 1A, 10B. The substrate was maintained at 300° C. Deposition was carried out for 40 minutes to form a 2,200 Å layer.

Example 13

Graded Silicon Germanium Carbon by ALD

The substrate was prepared as in Example 2. The wafer was loaded into the deposition chamber and subjected to a hydrogen purge for 10 minutes. A flow of carrier gas, argon, was directed towards the substrate and the source compounds were pulsed into this flow. ALD cycle included: $HCl_2SiCH_3$ (0.8 s), purge (1.0 s), $HCl_2SiGeH_3$ (0.8 s), purge (1.0 s). A film is grown by running cycles for a desired film thickness. The substrate was maintained at 500° C. Deposition was carried out for 40 minutes to form a 2,000 Å layer.

Example 14

Synthesis of $H_3SiSiCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Silane was supplied to reactor 1 at a rate of 15 L/min. Tetrachlorosilane was supplied to reactor 1 at a rate of 15 L/min. The outlet gas of reactor 2 was analyzed to find that the yields of silane compounds and silicon compounds including $H_3SiSiCl_3$.

Example 15

Synthesis of $H_3SiGeCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Silane was supplied to reactor 1 at a rate of 15 L/min. Tetrachlorogermane was supplied to reactor 1 at a rate of 15 L/min. The outlet gas of reactor 2 was analyzed to find that the yields of silane compounds and silicon compounds including $H_3SiGeCl_3$.

Example 16

Synthesis of $H_3GeSiCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Germane was supplied to reactor 1 at a rate of 15 L/min. Tetrachlorosilane was supplied to reactor 1 at a rate of 15

L/min. The outlet gas of reactor 2 was analyzed to find that the yields of silane compounds and silicon compounds including $H_3GeSiCl_3$.

Example 17

Synthesis of $F_3CSiCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Tetrafluoromethane was supplied to reactor 1 at a rate of 15 L/min. Tetrachlorosilane was supplied to reactor 1 at a rate of 15 L/min. The outlet gas of reactor 2 was analyzed to find that the yields of silane compounds and silicon compounds including $F_3CSiCl_3$.

THEORETICAL EXPERIMENTS 18-34 INCLUDING SILICON COMPOUNDS $Si_2RX_8$

Example 18

Monocrystalline Silicon by Selective CVD

A substrate, Si<100>, was employed to investigate selective, monocrystalline film growth by CVD. A silicon oxide feature existed on the surface of the wafer. The wafer was prepared by subjecting to a 0.5% HF dip for 30 seconds followed by baking at 750° C. for 60 seconds. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 30 sccm of $Cl_3SiSiH_2SiH_3$, was delivered to the chamber at 10 Torr and 750° C. The substrate was maintained at 750° C. Deposition was carried out for 3 minutes to form a 400 Å epitaxial layer on the silicon surface, but no epitaxial growth occurred on the silicon dioxide surface.

Example 19

Monocrystalline Silicon by Blanket CVD

A substrate, Si<100>, was employed to investigate blanket, monocrystalline film growth by CVD. A silicon oxide feature existed on the surface of the wafer. The wafer was prepared by subjecting to a 0.5% HF dip for 30 seconds followed by baking at 750° C. for 60 seconds. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 50 sccm of $Cl_3SiSiH_2SiH_3$, was added to the chamber at 100 Torr and 650° C. The substrate was maintained at 650° C. Deposition was carried out for 4 minutes to form a 1,600 Å epitaxial layer.

Example 20

Polysilicon by CVD

The substrate was prepared as in Example 19. The wafer was loaded into the deposition chamber (POLYGEN™ chamber) and subjected to a hydrogen purge for 2 minutes. A flow of carrier gas, hydrogen, was directed towards the substrate and the source compounds were added to the carrier flow. The silicon compound, 100 sccm of $HF_2SiSiH_2SiClH_2$, was added to the chamber at 80 Torr and 550° C. The substrate was maintained at 550° C. Deposition was carried out for 3 minutes to form a 1,200 Å layer.

Example 21

Amorphous Silicon by CVD

A silicon dioxide layered wafer was loaded into the deposition chamber (Epi CENTURA® chamber) and subjected to a hydrogen purge for 1 minute. A flow of carrier gas, hydrogen, was directed towards the substrate and the source compounds were added to the carrier flow. The silicon compound, 200 sccm of $HCl_2SiSiH_2SiH_3$, was added to the chamber at 200 Torr and 40° C. The substrate was maintained at 40° C. Deposition was carried out for 3 minutes to form a 200 Å layer.

Example 22

Silicon Germanium by CVD

The substrate was prepared as in Example 19. The wafer was loaded into the deposition chamber (Epi CENTURA® chamber) and subjected to a hydrogen purge for 1 minute. A flow of carrier gas, hydrogen, was directed towards the substrate and the source compounds were added to the carrier flow. The silicon compound, 10 sccm $HCl_2SiSiH_2GeH_3$, was added to the chamber at 100 Torr and 650° C. The substrate was maintained at 650° C. Deposition was carried out for 5 minutes to form a 600 Å epitaxial layer.

Example 23

Silicon Carbon by CVD

The substrate was prepared as in Example 19. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2CSiH_2SiH_3$, was added to the chamber at 100 Torr and 500° C. The substrate was maintained at 500° C. Deposition was carried out for 15 minutes to form a 1,400 Å epitaxial layer.

Example 24

Silicon Germanium Carbon by CVD

The substrate was prepared as in Example 19. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2SiSiH_2GeH_3$, was added to the chamber at 100 Torr and 550° C. The silicon compound, $H_3CSiH_2SiH_3$, was also added to the chamber at 2 sccm. The substrate was maintained at 550° C. Deposition was carried out for 10 minutes to form a 2,100 Å epitaxial layer.

Example 25

Doped Silicon CVD

The substrate was prepared as in Example 19. The wafer was loaded into the deposition chamber (Epi CENTURA™ chamber) and subjected to a hydrogen purge for 2 minutes. A flow of carrier gas, hydrogen, was directed towards the substrate and the source compounds were added to the carrier flow. The silicon compound, 100 sccm of $Cl_3SiSiH_2SiH_3$, was added to the chamber at 100 Torr and 750° C. The dopant compound, 1 sccm of 1000 ppm $B_2H_6$ in $H_2$, was also added to the chamber. The substrate was maintained at 750° C. Deposition was carried out for 3 minutes to form a 600 Å epitaxial doped layer.

Example 26

Graded Silicon Germanium by CVD

The substrate was prepared as in Example 19. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 50 sccm of $HCl_2SiSiH_2SiH_3$, was added to the chamber at 10 Torr and 650° C. A decreasing flow from 225 sccm down to 5 sccm of the silicon compound, $HCl_2SiSiH_2GeH_3$, was also added to the chamber during the deposition step. The flow rate was changed non-linearly in respect to time to produce a linearly graded final germanium content in the deposited film. The substrate was maintained at 550° C. Deposition was carried out for 5 minutes to form a 1,200 Å epitaxial layer.

Example 27

Graded Silicon Germanium Carbon by CVD

The substrate was prepared as in Example 19. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 100 sccm of $HCl_2SiSiH_2CH_3$, was added to the chamber at 10 Torr and 650° C. Also, 10 sccm of 5% $H_3CSiH_2SiH_3$ was added to the chamber. A decreasing flow from 350 sccm down to 5 sccm of the silicon compound, $HCl_2SiSiH_2GeH_3$, was also added to the chamber during the deposition step. The flow rate was changed non-linearly to produce a linearly graded final germanium content in the deposited film. The substrate was maintained at 550° C. Deposition was carried out for 5 minutes to form a 1,300 Å epitaxial layer.

Example 28

Monocrystalline Selective Silicon by CVD with use of HCl

The substrate was prepared as in Example 18. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2SiSiH_2SiH_3$, was added to the chamber at 10 Torr and 600° C. A 5 sccm flow of hydrogen chloride was also delivered to the chamber. The substrate was maintained at 600° C. Deposition was carried out for 8 minutes to form a 500 Å epitaxial layer on the silicon surface, but no epitaxial growth occurred on the silicon dioxide surface.

Example 29

Graded Silicon Germanium by ALD

The substrate was prepared as in Example 2. The wafer was loaded into the deposition chamber and subjected to a hydrogen purge for 10 minutes. A flow of carrier gas, argon, was directed towards the substrate and the source compounds were pulsed into this flow. The H-atoms are generated via a tungsten hot-wire. ALD cycle A included: $HCl_2SiSiH_2SiH_3$ (0.8 s), purge (1.0 s), H-atoms (1.2 s), purge (1.0 s). ALD cycle B included: $HCl_2SiSiH_2GeH_3$ (0.8 s), purge (1.0 s), H-atoms (1.2 s), purge (1.0 s). A graded film is grown by running a sequence of cycles such as: 10A, 1B, 5A, 1B, 1A, 1B, 1A, 5B, 1A, 10B. The substrate was maintained at 300° C. Deposition was carried out for 40 minutes to form a 2,200 Å layer.

Example 30

Graded Silicon Germanium Carbon by ALD

The substrate was prepared as in Example 19. The wafer was loaded into the deposition chamber and subjected to a hydrogen purge for 10 minutes. A flow of carrier gas, argon, was directed towards the substrate and the source compounds were pulsed into this flow. ALD cycle included: $HCl_2SiSiH_2CH_3$ (0.8 s), purge (1.0 s), $HCl_2SiSiH_2GeH_3$ (0.8 s), purge (1.0 s). A film is grown by running cycles for a desired film thickness. The substrate was maintained at 500° C. Deposition was carried out for 40 minutes to form a 2,000 Å layer.

Example 31

Synthesis of $H_3SiSiH_2SiCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Disilane was supplied to reactor 1 at a rate of 15 L/min. Tetrachlorosilane was supplied to reactor 1 at a rate of 15 L/min. The outlet gas of reactor 2 was analyzed to find that the yields of silane compounds and silicon compounds including $H_3SiSiH_2SiCl_3$.

Example 32

Synthesis of $H_3SiSiH_2GeCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Disilane was supplied to reactor 1 at a rate of 15 L/min. Tetrachlorogermane was supplied to reactor 1 at a rate of 15 L/min. The outlet gas of reactor 2 was analyzed to find that the yields of silane compounds and silicon compounds including $H_3SiSiH_2GeCl_3$.

Example 33

Synthesis of $H_3GeSiCl_2SiCl$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Germane was supplied to reactor 1 at a rate of 15 L/min. Hexachlorodisilane was supplied to reactor 1 at a rate of 15

L/min. The outlet gas of reactor 2 was analyzed to find that the yields of silane compounds and silicon compounds including $H_3GeSiCl_2SiCl_3$.

Example 34

Synthesis of $F_3CSiH_2SiH_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Tetrafluoromethane was supplied to reactor 1 at a rate of 15 L/min. Disilane was supplied to reactor 1 at a rate of 15 L/min. The outlet gas of reactor 2 was analyzed to find that the yields of silane compounds and silicon compounds including $F_3CSiH_2SiH_3$.

THEORETICAL EXPERIMENTS 35-56 INCLUDING SILICON COMPOUNDS FROM COMPOUNDS 1-32

Example 35

Monocrystalline Silicon by Selective CVD

A substrate, Si<100>, was employed to investigate selective, monocrystalline film growth by CVD. A silicon oxide feature existed on the surface of the wafer. The wafer was prepared by subjecting to a 0.5% HF dip for 30 seconds followed by baking at 750° C. for 60 seconds. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 30 sccm of $Cl_3SiSiH_2SiH_2SiH_3$, was delivered to the chamber at 10 Torr and 750° C. The substrate was maintained at 750° C. Deposition was carried out for 3 minutes to form a 400 Å epitaxial layer on the silicon surface, but no epitaxial growth occurred on the silicon dioxide surface.

Example 36

Monocrystalline Silicon by Blanket CVD

A substrate, Si<100>, was employed to investigate blanket, monocrystalline film growth by CVD. A silicon oxide feature existed on the surface of the wafer. The wafer was prepared by subjecting to a 0.5% HF dip for 30 seconds followed by baking at 750° C. for 60 seconds. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 50 sccm of $Cl_3SiSiH_2SiH_2SiH_3$, was added to the chamber at 100 Torr and 650° C. The substrate was maintained at 650° C. Deposition was carried out for 4 minutes to form a 1,600 Å epitaxial layer.

Example 37

Polysilicon by CVD

The substrate was prepared as in Example 36. The wafer was loaded into the deposition chamber (POLYGEN™ chamber) and subjected to a hydrogen purge for 2 minutes. A flow of carrier gas, hydrogen, was directed towards the substrate and the source compounds were added to the carrier flow. The silicon compound, 100 sccm of $HF_2SiSiH_2SiH_2SiH_2SiClH_2$, was added to the chamber at 80 Torr and 550° C. The substrate was maintained at 550° C. Deposition was carried out for 3 minutes to form a 1,200 Å layer.

Example 38

Amorphous Silicon by CVD

A silicon dioxide layered wafer was loaded into the deposition chamber (Epi CENTURA® chamber) and subjected to a hydrogen purge for 1 minute. A flow of carrier gas, hydrogen, was directed towards the substrate and the source compounds were added to the carrier flow. The silicon compound, 200 sccm of $HCl_2SiSiH_2SiH_2SiH_2SiH_3$, was added to the chamber at 200 Torr and 40° C. The substrate was maintained at 40° C. Deposition was carried out for 3 minutes to form a 200 Å layer.

Example 39

Silicon Germanium by CVD

The substrate was prepared as in Example 2. The wafer was loaded into the deposition chamber (Epi CENTURA® chamber) and subjected to a hydrogen purge for 1 minute. A flow of carrier gas, hydrogen, was directed towards the substrate and the source compounds were added to the carrier flow. The silicon compound, 10 sccm $HCl_2SiSiH_2SiH_2SiH_2GeH_3$, was added to the chamber at 100 Torr and 650° C. The substrate was maintained at 650° C. Deposition was carried out for 5 minutes to form a 600 Å epitaxial layer.

Example 40

Silicon Carbon by CVD

The substrate was prepared as in Example 2. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2CSiH_2SiH_2SiH_2SiH_3$, was added to the chamber at 100 Torr and 500° C. The substrate was maintained at 500° C. Deposition was carried out for 15 minutes to form a 1,400 Å epitaxial layer.

Example 41

Silicon Germanium Carbon by CVD

The substrate was prepared as in Example 36. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2SiSiH_2SiH_2GeH_3$, was added to the chamber at 100 Torr and 550° C. The silicon compound, $H_3CSiH_2SiH_2SiH_3$, was also added to the chamber at 2 sccm. The substrate was maintained at 550° C. Deposition was carried out for 10 minutes to form a 2,100 Å epitaxial layer.

Example 42

Doped Silicon CVD

The substrate was prepared as in Example 36. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 100 sccm of $Cl_3SiSiH_2SiH_2SiH_3$, was added to the chamber at 100 Torr and 750° C. The dopant compound, 1 sccm of 1000 ppm $B_2H_6$ in $H_2$, was also added to the chamber. The substrate was maintained at 750° C. Deposition was carried out for 3 minutes to form a 600 Å epitaxial doped layer.

Example 43

Graded Silicon Germanium by CVD

The substrate was prepared as in Example 36. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 50 sccm of $HCl_2SiSiH_2SiH_3$, was added to the chamber at 10 Torr and 650° C. A decreasing flow from 225 sccm down to 5 sccm of the silicon compound, $HCl_2SiSiH_2GeH_3$, was also added to the chamber during the deposition step. The flow rate was changed non-linearly in respect to time to produce a linearly graded final germanium content in the deposited film. The substrate was maintained at 550° C. Deposition was carried out for 5 minutes to form a 1,200 Å epitaxial layer.

Example 44

Graded Silicon Germanium Carbon by CVD

The substrate was prepared as in Example 36. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 100 sccm of $HCl_2SiSiH_2GeH_3$, was added to the chamber at 10 Torr and 650° C. Also, 10 sccm of 5% $H_3CSiH_2SiH_2SiH_3$ was added to the chamber. A decreasing flow from 350 sccm down to 5 sccm of the silicon compound, $HCl_2SiSiH_2SiH_2GeH_3$, was also added to the chamber during the deposition step. The flow rate was changed non-linearly to produce a linearly graded final germanium content in the deposited film. The substrate was maintained at 550° C. Deposition was carried out for 5 minutes to form a 1,300 Å epitaxial layer.

Example 45

Monocrystalline Selective Silicon by CVD with use of HCl

The substrate was prepared as in Example 35. The wafer was loaded into the deposition chamber (Epi CENTURA® chamber) and subjected to a hydrogen purge for 2 minutes. A flow of carrier gas, hydrogen, was directed towards the substrate and the source compounds were added to the carrier flow. The silicon compound, 10 sccm of $HCl_2SiSiH_2SiH_2SiH_3$, was added to the chamber at 10 Torr and 600° C. A 5 sccm flow of hydrogen chloride was also delivered to the chamber. The substrate was maintained at 600° C. Deposition was carried out for 8 minutes to form a 500 Å epitaxial layer on the silicon surface, but no epitaxial growth occurred on the silicon dioxide surface.

Example 46

Graded Silicon Germanium by ALD

The substrate was prepared as in Example 36. The wafer was loaded into the deposition chamber and subjected to a hydrogen purge for 10 minutes. A flow of carrier gas, argon, was directed towards the substrate and the source compounds were pulsed into this flow. The H-atoms are generated via a tungsten hot-wire. ALD cycle A included: $HCl_2SiSiH_2SiH_2SiH_3$ (0.8 s), purge (1.0 s), H-atoms (1.2 s), purge (1.0 s). ALD cycle B included: $HCl_2SiSiH_2SiH_2GeH_3$ (0.8 s), purge (1.0 s), H-atoms (1.2 s), purge (1.0 s). A graded film is grown by running a sequence of cycles such as: 10 A, 1 B. 5 A, 1 B, 1 A, 1 B, 1 A, 5 B, 1 A, 10 B. The substrate was maintained at 300° C. Deposition was carried out for 40 minutes to form a 2,200 Å layer.

Example 47

Graded Silicon Germanium Carbon by ALD

The substrate was prepared as in Example 36. The wafer was loaded into the deposition chamber and subjected to a hydrogen purge for 10 minutes. A flow of carrier gas, argon, was directed towards the substrate and the source compounds were pulsed into this flow. ALD cycle included: $HCl_2SiSiH_2SiH_2GeH_3$ (0.8 s), purge (1.0 s), $HCl_2SiSiH_2SiH_2CH_3$ (0.8 s), purge (1.0 s). A film is grown by running cycles for a desired film thickness. The substrate was maintained at 500° C. Deposition was carried out for 40 minutes to form a 2,000 Å layer.

Example 48

Synthesis of $H_3SiSiH_2SiCl_2SiCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Disilane was supplied to reactor 1 at a rate of 15 L/min. Hexachlorodisilane was supplied to reactor 1 at a rate of 15 L/min. The outlet gas of reactor 2 was analyzed to find that the yields of silane compounds and silicon compounds including $H_3SiSiH_2SiCl_2SiCl_3$.

Example 49

Synthesis of $H_3SiSiH_2SiH_2GeCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Trisilane was supplied to reactor 1 at a rate of 15 L/min. Tetrachlorogermane was supplied to reactor 1 at a rate of 15

L/min. The outlet gas of reactor 2 was analyzed to find that the yields of silane compounds and silicon compounds including $H_3SiSiH_2SiH_2GeCl_3$.

Example 50

Synthesis of $Cl_3SiSiCl_2SiCl_2GeH_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Germane was supplied to reactor 1 at a rate of 15 L/min. Octachlorotrisilane was supplied to reactor 1 at a rate of 15 L/min. The outlet gas of reactor 2 was analyzed to find that the yields of silane compounds and silicon compounds including $Cl_3SiSiCl_2SiCl_2GeH_3$.

Example 51

Synthesis of $F_3CSiH_2SiH_2SiH_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Tetrafluoromethane was supplied to reactor 1 at a rate of 15 L/min. Trisilane was supplied to reactor 1 at a rate of 15 L/min. The outlet gas of reactor 2 was analyzed to find that the yields of silane compounds and silicon compounds including $F_3CSiH_2SiH_2SiH_3$.

Example 52

Synthesis of $H_3SiSiH_2SiH_2SiCl_2SiCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Trisilane was supplied to reactor 1 at a rate of 15 L/min. Hexachlorodisilane was supplied to reactor 1 at a rate of 15 L/min. The outlet gas of reactor 2 was analyzed to find that the yields of silane compounds and silicon compounds including $H_3SiSiH_2SiH_2SiCl_2SiCl_3$.

Example 53

Synthesis of $H_3SiSiH_2SiH_2SiH_2GeCl_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Tetrasilane was supplied to reactor 1 at a rate of 15 L/min. Tetrachlorogermane was supplied to reactor 1 at a rate of 15 L/min. The outlet gas of reactor 2 was analyzed to find that the yields of silane compounds and silicon compounds including $H_3SiSiH_2SiH_2SiH_2GeCl_3$.

Example 54

Synthesis of $Cl_3SiSiCl_2SiCl_2SiCl_2GeH_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Decachlorotetrasilane was supplied to reactor 1 at a rate of 15 L/min. Germane was supplied to reactor 1 at a rate of 15 L/min. The outlet gas of reactor 2 was analyzed to find that the yields of silane compounds and silicon compounds including $Cl_3SiSiCl_2SiCl_2SiCl_2GeH_3$.

Example 55

Synthesis of $F_3CSiH_2SiH_2SiH_2SiH_3$

A 2.5 L SUS (reactor 1) and a 5 L SUS (reactor 2) were connected in the direct series, the inside temperature of reactor 1 was set to 450° C. and the inside temperature of reactor 2 was set to 350° C. The pressure was set to 0.13 MPa. Tetrafluoromethane was supplied to reactor 1 at a rate of 15 L/min. Tetrasilane was supplied to reactor 1 at a rate of 15 L/min. The outlet gas of reactor 2 was analyzed to find that the yields of silane compounds and silicon compounds including $F_3CSiH_2SiH_2SiH_2SiH_3$.

While the foregoing is directed to embodiments of the present invention, other and further embodiments of the invention may be devised without departing from the basic scope thereof, and the scope thereof is determined by the claims that follow.

The invention claimed is:

1. A method for selectively and epitaxially depositing a silicon-containing material on a substrate, comprising:
    positioning a substrate comprising a crystalline surface and a non-crystalline surface within a process chamber;
    heating the substrate to a predetermined temperature;
    exposing the substrate to a process gas comprising a silicon source selected from the group consisting of isotetrasilane, cyclic-tetrasilane, cyclic pentasilane, and neopentasilane; and
    depositing an epitaxial layer on the crystalline surface.

2. The method of claim 1, wherein the predetermined temperature is about 600° C.

3. The method of claim 2, wherein the epitaxial layer is a silicon epitaxial layer.

4. The method of claim 3, wherein the process gas further comprises hydrogen gas, a germanium source, a dopant source, or combinations thereof.

5. The method of claim 3, wherein the silicon epitaxial layer comprises a phosphorus concentration within a range from about $10^{19}$ atoms/cm$^3$ to about $10^{21}$ atoms/cm$^3$.

6. The method of claim 1, wherein the process gas further comprises a carbon source.

7. The method of claim 6, wherein the carbon source is selected from the group consisting of a silicon carbon source, an alkane source, an alkene source, an alkyne source, derivatives thereof, and combinations thereof.

8. The method of claim 7, wherein the carbon source is a silicon carbon source comprising the chemical formula:

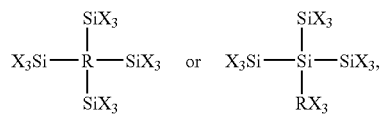

wherein R is carbon and X is hydrogen.

9. The method of claim 6, wherein the carbon source is methylsilane.

10. The method of claim 6, wherein the epitaxial layer comprises silicon carbide.

11. The method of claim 10, wherein the epitaxial layer comprises a carbon concentration of about 5 at % or less.

12. The method of claim 11, wherein the carbon concentration is within a range from about 200 ppm to about 2 at %.

13. The method of claim 1, wherein the non-crystalline surface comprises dielectric features further comprising an oxide material, a nitride material, or combinations thereof.

14. The method of claim 13, wherein the dielectric features are left bare immediately after depositing the epitaxial layer.

15. The method of claim 13, wherein the dielectric features remain covered after immediately depositing the epitaxial layer.

16. The method of claim 1, wherein the substrate is exposed to a HF solution during a pretreatment process prior to depositing the epitaxial layer.

17. The method of claim 16, wherein the pretreatment process further comprises heating the substrate to about 800° C. within a hydrogen atmosphere after the HF solution exposure.

18. A method for blanket depositing a silicon-containing material on a substrate, comprising:
    positioning a substrate containing a crystalline surface and at least one feature surface within a process chamber, wherein the at least one feature surface comprises an oxide material, a nitride material, or combinations thereof;
    heating the substrate to a predetermined temperature;
    exposing the substrate to a process gas comprising a silicon source selected from the group consisting of isotetrasilane, cyclic-tetrasilane, cyclic pentasilane, and neopentasilane; and
    depositing a silicon-containing blanket layer across the crystalline surface and the feature surfaces, wherein the silicon-containing blanket layer comprises a silicon-containing epitaxial layer selectively deposited on the crystalline surface.

19. A method for blanket depositing a silicon-containing material on a substrate, comprising:
    positioning a substrate comprising a crystalline surface and feature surfaces within a process chamber;
    heating the substrate to a predetermined temperature;
    exposing the substrate to a process gas comprising a silicon source selected from the group consisting of isotetrasilane, cyclic-tetrasilane, cyclic pentasilane, and neopentasilane and a carbon source; and
    depositing a silicon carbide blanket layer across the crystalline surface and the feature surfaces, wherein the silicon carbide blanket layer comprises a silicon carbide epitaxial layer selectively deposited on the crystalline surface.

20. The method of claim 19, wherein the silicon carbide epitaxial layer comprises a carbon concentration of about 5 at % or less.

21. The method of claim 20, wherein the carbon concentration is within a range from about 200 ppm to about 2 at %.

22. The method of claim 21, wherein the carbon source is selected from the group consisting of a silicon carbon source, an alkane source, an alkene source, an alkyne source, derivatives thereof, and combinations thereof.

23. The method of claim 21, wherein the carbon source is methylsilane.

24. The method of claim 19, wherein the process gas further comprises hydrogen gas, a germanium source, a dopant source, or combinations thereof.

25. The method of claim 19, wherein the silicon carbide epitaxial layer comprises a phosphorus concentration within a range from about $10^{19}$ atoms/cm$^3$ to about $10^{21}$ atoms/cm$^3$.

26. The method of claim 19, wherein the feature surfaces comprise oxides, nitrides, or combinations thereof.

27. The method of claim 26, wherein the feature surfaces are left bare immediately after depositing the epitaxial layer.

28. The method of claim 26, wherein the feature surfaces remain covered immediately after depositing the epitaxial layer.

29. The method of claim 1, wherein the silicon source comprises isotetrasilane.

30. The method of claim 18, wherein the silicon source comprises isotetrasilane.

31. The method of claim 19, wherein the silicon source comprises isotetrasilane.

* * * * *

UNITED STATES PATENT AND TRADEMARK OFFICE
CERTIFICATE OF CORRECTION

PATENT NO. : 7,645,339 B2 Page 1 of 1
APPLICATION NO. : 11/549033
DATED : January 12, 2010
INVENTOR(S) : Kaushal K. Singh et al.

It is certified that error appears in the above-identified patent and that said Letters Patent is hereby corrected as shown below:

Cover Page, (63) Related U.S. Application Data, delete "filed on Oct. 17, 2003, now abandoned" and insert --now U.S. patent 7,540,920,--.

Signed and Sealed this

Sixteenth Day of March, 2010

David J. Kappos
*Director of the United States Patent and Trademark Office*